US009956169B2

(12) United States Patent
Tian et al.

(10) Patent No.: US 9,956,169 B2
(45) Date of Patent: May 1, 2018

(54) ORAL VACCINE FAST-DISSOLVING DOSAGE FORM USING STARCH

(75) Inventors: Wei Tian, Minety (GB); Rosie McLaughlin, Swindon (GB)

(73) Assignee: R.P. SCHERER TECHNOLOGIES, LLC, Las Vegas, NV (US)

( * ) Notice: Subject to any disclaimer, the term of this patent is extended or adjusted under 35 U.S.C. 154(b) by 0 days. days.

(21) Appl. No.: 13/270,411

(22) Filed: Oct. 11, 2011

(65) Prior Publication Data

US 2012/0087944 A1 Apr. 12, 2012

Related U.S. Application Data

(60) Provisional application No. 61/391,238, filed on Oct. 8, 2010.

(51) Int. Cl.

| | |
|---|---|
| ***A61K 9/00*** | (2006.01) |
| ***A61K 39/12*** | (2006.01) |
| ***C12N 7/00*** | (2006.01) |
| ***A61K 9/20*** | (2006.01) |
| ***A61K 39/145*** | (2006.01) |
| ***A61K 39/00*** | (2006.01) |

(52) U.S. Cl.

CPC ............ *A61K 9/006* (2013.01); *A61K 9/0056* (2013.01); *A61K 9/2095* (2013.01); *A61K 39/12* (2013.01); *A61K 39/145* (2013.01); *C12N 7/00* (2013.01); *A61K 2039/542* (2013.01); *A61K 2039/55583* (2013.01); *A61K 2039/57* (2013.01); *A61K 2039/6087* (2013.01); *C12N 2760/16134* (2013.01); *C12N 2760/16151* (2013.01)

(58) Field of Classification Search

CPC .. A61K 2039/55583; A61K 2039/6087; A61K 39/145; A61K 9/0056; A61K 9/006; A61K 9/2095; A61K 9/4891; C12N 2760/16134; C12N 2760/16151; C12N 7/00

See application file for complete search history.

(56) References Cited

U.S. PATENT DOCUMENTS

| | | | | |
|---|---|---|---|---|
| 4,371,516 A | 2/1983 | Gregory et al. | | |
| 5,079,018 A * | 1/1992 | Ecanow | A23C 1/08 | 424/602 |
| 5,472,704 A | 12/1995 | Santus et al. | | |
| 5,976,577 A * | 11/1999 | Green | A61K 9/0056 | 424/400 |
| 6,316,027 B1 * | 11/2001 | Johnson | A61K 9/0056 | 424/464 |
| 6,342,246 B2 * | 1/2002 | Johnson | 424/434 | |
| 6,413,549 B2 * | 7/2002 | Green | A61K 9/0056 | 424/484 |
| 6,509,040 B1 * | 1/2003 | Murray | A61K 47/36 | 424/400 |
| 6,709,669 B1 * | 3/2004 | Murray | A61K 9/0056 | 424/434 |
| 7,393,928 B2 | 7/2008 | Chang et al. | | |
| 7,884,083 B2 | 2/2011 | Van Nest et al. | | |
| 7,972,621 B2 * | 7/2011 | Wong | A61K 9/0056 | 424/451 |
| 8,012,505 B2 * | 9/2011 | Houghton | A61K 9/006 | 424/484 |
| 8,329,196 B2 | 12/2012 | Jacobi et al. | | |
| 8,481,045 B2 | 7/2013 | Swartz et al. | | |
| 8,545,879 B2 * | 10/2013 | Burns | A61K 9/0056 | 424/456 |
| 9,192,580 B2 * | 11/2015 | Green | A61K 9/0056 | |
| 2002/0034542 A1 * | 3/2002 | Thombre | A61K 9/0056 | 424/465 |
| 2003/0064074 A1 | 4/2003 | Chang et al. | | |
| 2004/0013695 A1 * | 1/2004 | Vande-Velde | 424/400 | |
| 2004/0076666 A1 * | 4/2004 | Green | A61K 9/0056 | 424/465 |
| 2004/0166123 A1 | 8/2004 | Jacobi et al. | | |
| 2004/0247648 A1 * | 12/2004 | Fadden | A61K 9/006 | 424/440 |
| 2004/0265377 A1 * | 12/2004 | Seager | 424/464 | |
| 2007/0014807 A1 | 1/2007 | Maida, III | | |
| 2008/0014260 A1 | 1/2008 | Seager | | |
| 2008/0187558 A1 | 8/2008 | Jacobi et al. | | |
| 2008/0193535 A1 | 8/2008 | Jacobi et al. | | |
| 2009/0017075 A1 | 1/2009 | Van Nest et al. | | |
| 2009/0143568 A1 | 6/2009 | Chang et al. | | |
| 2009/0155351 A1 | 6/2009 | Hejl et al. | | |

(Continued)

FOREIGN PATENT DOCUMENTS

| | | |
|---|---|---|
| CN | 1120310 A | 4/1996 |
| CN | 1674878 A | 9/2005 |

(Continued)

OTHER PUBLICATIONS

Goodgame RW. Viral infections of the gastrointestinal tract. Curr Gastroenterol Rep. Aug. 1999;1(4):292-300.*
Leclerc H, Schwartzbrod L, Dei-Cas E. Microbial agents associated with waterborne diseases. Crit Rev Microbiol. 2002;28(4):371-409.*
McHardy IH, Li X, Tong M, Ruegger P, Jacobs J, Borneman J, Anton P, Braun J. HIV Infection is associated with compositional and functional shifts in the rectal mucosal microbiota. Microbiome. Oct. 12, 2013;1(1):26.*
Dey P, Maiti S. Orodispersible tablets: A new trend in drug delivery. J Nat Sci Biol Med. Jul. 2010;1(1):2-5.*
Habib W, Khankari R, Hontz J. Fast-dissolve drug delivery systems. Crit Rev Ther Drug Carrier Syst. 2000;17(1):61-72.*
Mestecky J. The common mucosal immune system and current strategies for induction of immune responses in external secretions. J Clin Immunol. Jul. 1987;7(4):265-76.*

(Continued)

*Primary Examiner* — Rachel B Gill
(74) *Attorney, Agent, or Firm* — Fitzpatrick, Cella, Harper & Scinto

(57) ABSTRACT

A fast-dissolving dosage form (FDDF) for the delivery of a vaccine is prepared using a formulation containing a starch, optionally, along with at least one additional matrix forming agent, preferably, a combination of gelatin and mannitol, where an immune response is induced in a patient in need thereof.

46 Claims, 7 Drawing Sheets

(56) References Cited

U.S. PATENT DOCUMENTS

| | | | | |
|---|---|---|---|---|
| 2009/0226522 | A1* | 9/2009 | Howes | A61K 9/06 424/484 |
| 2009/0311334 | A1* | 12/2009 | Lin | A61K 31/785 424/490 |
| 2010/0183655 | A1 | 7/2010 | Swartz et al. | |
| 2011/0059130 | A1* | 3/2011 | Yusibov | A61K 39/0216 424/210.1 |
| 2011/0129438 | A1 | 6/2011 | Swartz et al. | |
| 2011/0305768 | A1* | 12/2011 | Mao | A61K 39/15 424/499 |
| 2012/0034253 | A1* | 2/2012 | Yusibov | A61K 39/145 424/186.1 |
| 2012/0071538 | A1* | 3/2012 | Nilsson | A61K 9/0056 514/423 |
| 2012/0219628 | A1* | 8/2012 | Lim | A61K 9/0056 424/484 |
| 2013/0039932 | A1* | 2/2013 | Park | A61K 9/0056 424/184.1 |
| 2013/0089570 | A1 | 4/2013 | Ouaked et al. | |
| 2013/0108762 | A1* | 5/2013 | Mo et al. | 426/548 |
| 2014/0271722 | A1* | 9/2014 | Jacobi | A61K 9/0056 424/275.1 |
| 2016/0324767 | A1* | 11/2016 | Jacobi | A61K 9/0056 |

FOREIGN PATENT DOCUMENTS

| | | | |
|---|---|---|---|
| EP | 0516141 | A1 | 12/1992 |
| EP | 1579851 | A2 | 9/2005 |
| GB | 1548022 | A | 7/1979 |
| JP | 2001-521007 | A | 11/2001 |
| JP | 2003-513988 | A | 4/2003 |
| JP | 2004-506020 | A | 2/2004 |
| JP | 2006-513269 | A | 4/2006 |
| JP | 2007-504237 | A | 3/2007 |
| JP | 2009-510136 | A | 3/2009 |
| WO | 94/20070 | A1 | 9/1994 |
| WO | WO9713531 | * | 4/1997 |
| WO | 99/21579 | A1 | 5/1999 |
| WO | WO0044351 | * | 8/2000 |
| WO | WO2001034801 | * | 5/2001 |
| WO | 02/13858 | A1 | 2/2002 |
| WO | WO03/094886 | * | 11/2003 |
| WO | 2004014322 | A2 | 2/2004 |
| WO | 2004/047794 | A2 | 6/2004 |
| WO | 2005037190 | A2 | 4/2005 |
| WO | 2007038926 | A1 | 4/2007 |
| WO | 2008002663 | A2 | 1/2008 |
| WO | 2011151431 | A1 | 12/2011 |

OTHER PUBLICATIONS

Azizi A, Ghunaim H, Diaz-Mitoma F, Mestecky J. Mucosal HIV vaccines: a holy grail or a dud? Vaccine. May 28, 2010;28(24):4015-26. Epub Apr. 20, 2010.*

Dahiya M, Saha S, Shahiwala AF. A review on mouth dissolving films. Curr Drug Deliv. Oct. 2009;6(5):469-76.*

Kathpalia H, Gupte A. An introduction to fast dissolving oral thin film drug delivery systems: a review. Curr Drug Deliv. Dec. 2013;10(6):667-84.*

International Search Report issued in corresponding application No. PCT/US2011/055689 dated Jan. 16, 2012 (4 pages).

International Preliminary Report on Patentability issued in corresponding application No. PCT/US2011/055689 dated Apr. 9, 2013 (7 pages).

Seager, "Drug-delivery Products and the Zydis Fast-dissolving Dosage Form," J. Pharm. Pharmacol., vol. 50, pp. 375-382 (1998).

Wilson et al., "The behaviour of a fast-dissolving dosage form (Expidet) followed by gamma-scintigraphy," International Journal of Pharmaceutics, vol. 40, pp. 119-123 (1987).

Notice of Reasons for Rejection issued in Japanese Application No. 2013-533011, dated Sep. 7, 2015 (5 pages).

First Office Action issued in Chinese Application No. 201180059059.2, dated Aug. 5, 2014 (11 pages).

Second Office Action issued in Chinese Application No. 201180059059.2, dated Apr. 21, 2015 (12 pages).

Search Report issued in Chinese Application No. 201180059059.2, dated Jul. 28, 2014 (3 pages).

* cited by examiner

% bodyweight change following infection

- 1 - formulation 8
- 2 - Formulation 7
- 3 - Formulation 10
- 4 - Formulation 4
- 5 - Formulation 12
- Infected Control Clinical disease scores following infection with H1N1 Virus

- 1 - formulation 8
- 2 - Formulation 7
- 3 - Formulation 10
- 4 - Formulation 4
- 5 - Formulation 12
- Infected Control

ORAL VACCINE FAST-DISSOLVING DOSAGE FORM USING STARCH

This application claims the benefit of U.S. Provisional Patent Application No. 61/391,238, filed Oct. 8, 2010, the entire disclosure of which is incorporated by reference herein.

TECHNICAL FIELD

The invention relates to a fast-dissolving dosage form (FDDF) comprising a starch as an immune response potentiating matrix forming agent for the delivery of a vaccine. More specifically, the invention relates to an FDDF containing a starch and, optionally, mannitol and gelatin as additional matrix forming agents for the delivery of an oral vaccine to stimulate immunity to infection caused by bacteria, viruses such as influenza, other microorganisms or parasites such as protozoa or worms.

BACKGROUND

A large variety of dosage forms for oral ingestion are known and readily available in the medical field. The most common of these is the tablet. The main limitations of pharmaceutical tablets include poor patient compliance due to difficulty in swallowing and lack of bioavailability of the active through ineffective dissolution of the tablet.

Fast-dissolving dosage forms (FDDFs) are convenient to use and are often used to address issues of patient compliance. There are many forms of FDDFs, for example, "loosely" compressed tablets comprising a large amount of wicking/disintegrating agents, tablets comprising a large amount of effervescent agents, and lyophilized tablets. Most commonly, lyophilized, fast-dissolving dosage forms, which are designed to release the active ingredient in the oral cavity, are formulated using rapidly soluble gelatin-based matrices. These dosage forms are well known and can be used to deliver a wide range of drugs. Most fast-dissolving dosage forms utilize gelatin and mannitol as carriers or matrix forming agents. (Seagar, H., "Drug-Delivery Products and Zydis Fast Dissolving Dosage Form," *J. Pharm. Pharmaco*, vol. 50, p. 375-382 (1998)).

FDDFs manufactured by the freeze-drying process such as the Zydis® dosage form are often preferred. They have the distinct advantages of a faster disintegrating time (i.e., less than 5 seconds, as opposed to 1 minute for the loosely compressed tablets), smoother mouth feel (i.e., free of the grittiness associated with the high wicking agents in the compressed tablets), potential for improved pregastric absorption (thereby reduced side effects and improved efficacy for certain medications), and increased storage options.

Typically, gelatin is used to give sufficient strength to the dosage form to prevent breakage during removal from packaging, but once placed in the mouth, the gelatin allows immediate dispersion of the dosage form. Hydrolyzed mammalian gelatin is often the matrix forming agent of choice in FDDFs because it gels rapidly upon cooling. Non-gelling fish gelatin may also be used. During processing, dosed solution/suspension is preferably frozen by passing through a gaseous medium. Thereby, the solution/suspension freezes rapidly, which improves the manufacturing efficiency.

Vaccines, which are important in prophylaxis against disease, exert their effects by provoking an immune response, the effect of which is to prevent infection by the challenging organism, or the onset of the disease processes which would otherwise occur when the antigen against which the immune response has been provoked again challenges a sensitive tissue. Vaccines may also be used therapeutically to modify the nature or level of the immune response to an antigen to allow a host to eliminate a pathogen to which it has already been exposed.

Most existing vaccines are delivered by injection, which is traumatic, inconvenient, expensive and may fail to induce an appropriate immunogenic response in the mucosal tissues. The majority of infections affect, or start, in the mucosal surfaces. Active immunization against these infective agents can depend on the successful induction of a mucosal immune response. Successful mucosal vaccines can both protect the secretory surfaces, i.e., mucosal immunity, and also induce systemic immunity by induction of circulatory antibodies. Mucosal vaccines are also easier to administer to patients and are less expensive to manufacture than conventional vaccines. Delivery by injection does not, of course, directly target the mucosal surfaces or afford the advantages associated with oral vaccines.

The induction of mucosal immunity is evidenced by the appearance of immunoglobulins (Ig), of which IgA antibodies in the mucous overlying the mucosa are particularly significant. IgA exerts multiple effects within the mucosa. Most notably, it acts to neutralize pathogens and components of pathogens, preventing them from accessing and penetrating the underlying epithelial layers, which is what causes an infection. Stimulation of immunity at one mucosal site is known to confer protection to mucous membranes at other sites in the body. Potentially, oral vaccines can be used to induce immunity against oral, gastrointestinal, respiratory, urogenital and ocular pathogens. This ability to generate immunity at sites in the body away from the point of original antigenic stimulation has led to the concept of a common mucosal immune system. There are further indications that stimulation of the mucosal immune system can induce protective circulatory antibodies in the systemic immune system, particularly IgG antibodies. Optimal mucosal vaccines should also induce responses of T lymphocytes, such as the production of T helper cells that can support antibody production, and, for particular pathogens, Th17, Th1, Th2 cells and cytotoxic T lymphocytes (CTL) that act locally and/or systemically.

Vaccines delivered orally can stimulate nasal-associated lymphoid tissue in the mouth and nasopharyngeal region, the lymph nodes, tonsils and adenoids, and gut-associated lymphoid tissue in the Peyer's patches in the small intestine.

Vaccines incorporate antigens which can be peptides, proteins, polysaccharides or whole or partial fragments or extracts of bacteria, viruses or other microorganisms, often attenuated to remove toxic components. In order for vaccines to produce the desired protective effect, exposure to the antigen must be sufficient to provoke an immune response in the recipient. A primary problem in vaccination procedures is ensuring that these antigens or antigenic compounds reach the appropriate site in sufficient quantities to provoke the requisite immune response. There are two aspects of the immune system which can provide the requisite immune response when stimulated by an antigen in a vaccine system: the systemic immune system and the mucosal immune system.

The mucosal immune system consists of areas of inductive and effector lymphoid tissues located in the gastrointestinal tract, the respiratory tract, the genitourinary tract, and the membranes surrounding sensory organs. Inductive sites usually have an organized lymphoid structure and the ability to detect the presence of antigens in the mucosa. Antigen presenting cells at localized areas of lymphoid tissue have the ability to take up absorbed antigen and stimulate T and B cell responses resulting in the production of plasma cells. These plasma cells may reside locally or at effector sites throughout the body secreting antibodies, such as IgA. Secreted IgA molecules resist proteolysis and prevent colonization and entry of pathogens by neutralizing or agglutinating them. In other situations, IgA molecules activate antibody-dependent T cell mediated cytotoxicity, in cases where a pathogen has penetrated the initial barrier. Stimulation of mucosal tissue can also result in the production of other antibody isotypes, such as IgG, IgM, and IgE. These other antibody isotypes may exert effects locally in the mucosa, or have systemic effects, thereby providing additional protection if pathogens manage to penetrate the mucosa. T cell responses induced in the mucosa also can be present at mucosal sites or systemically, which enhances protection of mucosal surfaces and protection against pathogens that penetrate the mucosa.

The principal function of the cells forming the lymphoid tissue is to prevent absorption of pathogens and toxins or to inactivate these pathogens and toxins upon absorption to mucosal tissue. In general, considerably higher doses of antigens are required for mucosal immunization, especially when intended for the oral route. This is due to the existence of effective mechanical and chemical barriers and the degradation and digestion of antigens by enzymes and acids. Additionally, there is a rapid clearance of material from the upper respiratory and digestive tracts to the stomach by mucociliary, peristaltic and secretory processes.

The mucosa has evolved to prevent the induction of effector immune responses against harmless antigens such as foods and inhaled particles. Consequently, many antigens that are introduced at mucosal surfaces induce "tolerance" rather than productive T and B cell responses. Therefore, there is a need to overcome these natural processes in order to make effective vaccines.

Difficulty has been encountered in preparing oral solid dosage forms to deliver vaccines through the mucosal route while at the same time preserving ease of administration and patient comfort. Certain patients that have difficulty swallowing are typically poor candidates for solid oral vaccines with increased physical residency in the oral cavity of the dosage form.

Commercially available oral vaccines are either live attenuated vaccines (e.g., polio, typhoid, rotavirus) or inactivated vaccines (e.g., cholera) and are effective at eliciting an appropriate mucosal immune response since their natural site of infection is the gut mucosa and the vaccine unit triggers the body's natural immune defense mechanisms. However, effective and safe oral vaccines of sub-unit vaccines (containing antigenic fragments of microbes), toxoid vaccines or conjugate vaccines have not yet been established. Oral delivery of these peptide based vaccine strategies are significantly hindered due to their degradation on exposure to the acidic environment of the stomach and proteolytic enzymes that reside in the gastrointestinal tract (GIT). Also, the antigen generally is too large to diffuse across the mucosa of the GIT into the systemic circulation and fails to undergo active transport into the systemic circulation. Therefore, there is often insufficient antigen remaining to illicit either a systemic or mucosal immune response. In addition, a pre-requisite of a mucosal response within the GIT is uptake of the antigens by antigen presenting cells (APCs). The uptake of soluble antigens by the APCs is much less efficient than that of antigen microparticles. Therefore, soluble antigens often fail to achieve an adequate immune response, which can, in fact, lead to tolerance to the antigen.

Various strategies have been employed to protect the antigens from the harsh environment of the GIT and to facilitate a mucosal response. These include enveloping the antigen in liposomes, immunostimulatory complexes (ISCOMs), proteosomes and microparticles. However, such strategies can still require very high doses of antigen to be delivered, along with co-administration of mucosal adjuvants in order to elicit an effective humoral antibody and cell mediated response. Still further, many of the adjuvants under study, such as cholera toxin, are highly toxic in humans. These problems exist regardless of the source of the antigen (bacterial, viral, parasite, etc.).

Accordingly, there exists a need in the pharmaceutical field for improved oral vaccine dosage forms that effectively deliver immunogenic quantities of antigenic preparations and resist chemical and mechanical barriers to antigenic absorption. There further exists a need for solid oral dosage forms that can induce the immune response as effectively as an injectable vaccine while being easy to manufacture and easy and comfortable to administer.

U.S. Patent Application Publication No. 2008-0014260 discloses an oral solid fast-dispersing dosage form for the delivery of vaccines. However, the publication discloses an FDDF comprised of mannitol and gelatin as matrix forming agents. U.S. Pat. No. 6,509,040 teaches a pharmaceutical composition for oral administration in the form of a fast dispersing dosage form essentially free of mammalian gelatin and comprising at least one matrix forming agent and a starch. Neither of these references teaches or suggests the benefits achieved by the present invention, specifically the immune potentiating effect of starch.

The present invention is a novel formulation of FDDF using a starch as an immune response potentiating matrix forming agent, along with optional additional matrix forming agents such as mannitol and gelatin, to stimulate immunity to infection caused by bacteria, viruses, or other microorganisms and achieve better immune response than FDDF formulations known in the art. The immune potentiating effect of starch described in the present invention was not previously disclosed or suggested in the art. Also, the immune potentiating effect can be further enhanced by certain additional matrix forming agents or components, which, too, was not previously disclosed or suggested in the art. This is a significant advancement in the state of the art.

SUMMARY OF THE INVENTION

The present invention is directed to a fast-dissolving oral solid vaccine dosage form comprising: (a) an immunogenic amount of an antigenic preparation; and (b) at least one immune response potentiating matrix forming agent, wherein the at least one immune response potentiating matrix forming agent is a starch. In a preferred embodiment of the invention, the antigenic preparation comprises an inactivated influenza virus.

In certain preferred embodiments, the starch is present in the fast-dissolving oral solid vaccine dosage form in an amount of about 2% to about 90% by weight and/or is selected from the group consisting of native starch, modified starch and combinations thereof. In a preferred embodiment of the invention, the dosage form disintegrates within 60 seconds, more preferably within 30 seconds, still more preferably within 10 seconds, and most preferably within 5 seconds, after being placed in the oral cavity.

The fast-dissolving oral solid vaccine dosage forms of the present invention are preferably prepared by freeze-drying. The fast-dissolving oral solid vaccine dosage forms may comprise additional matrix forming agents such as mannitol and/or gelatin. In additional embodiments, the fast-dissolving oral solid vaccine dosage forms may further comprise at least one additional matrix forming agent selected from the group consisting of gums, preferably, xanthan gum, or a surfactant, preferably, Tween 80 (polysorbate 80) or poloxamer. The fast-dissolving oral solid vaccine dosage forms may comprise an adjuvant and/or a mucoadhesive.

In preferred embodiments of the invention, an immune response, e.g., an influenza specific antibody response, is induced when the fast-dissolving oral solid vaccine dosage form is administered to a patient by placement in the oral cavity. Preferably, placement in the oral cavity is placement on or under the tongue or in the buccal or pharyngeal region.

The present invention is also directed to a method of inducing an immune response, e.g., an influenza specific antibody response, in a patient, said method comprising the step of: placing the fast-dissolving oral solid vaccine dosage form comprising: (a) an immunogenic amount of an antigenic preparation; and (b) at least one immune response potentiating matrix forming agent, wherein the at least one immune response potentiating matrix forming agent is a starch, in the oral cavity of a person in need of the immune response. Preferably, placement in the oral cavity is placement on or under the tongue or in the buccal or pharyngeal region.

DETAILED DESCRIPTION OF THE INVENTION

Figure 1:
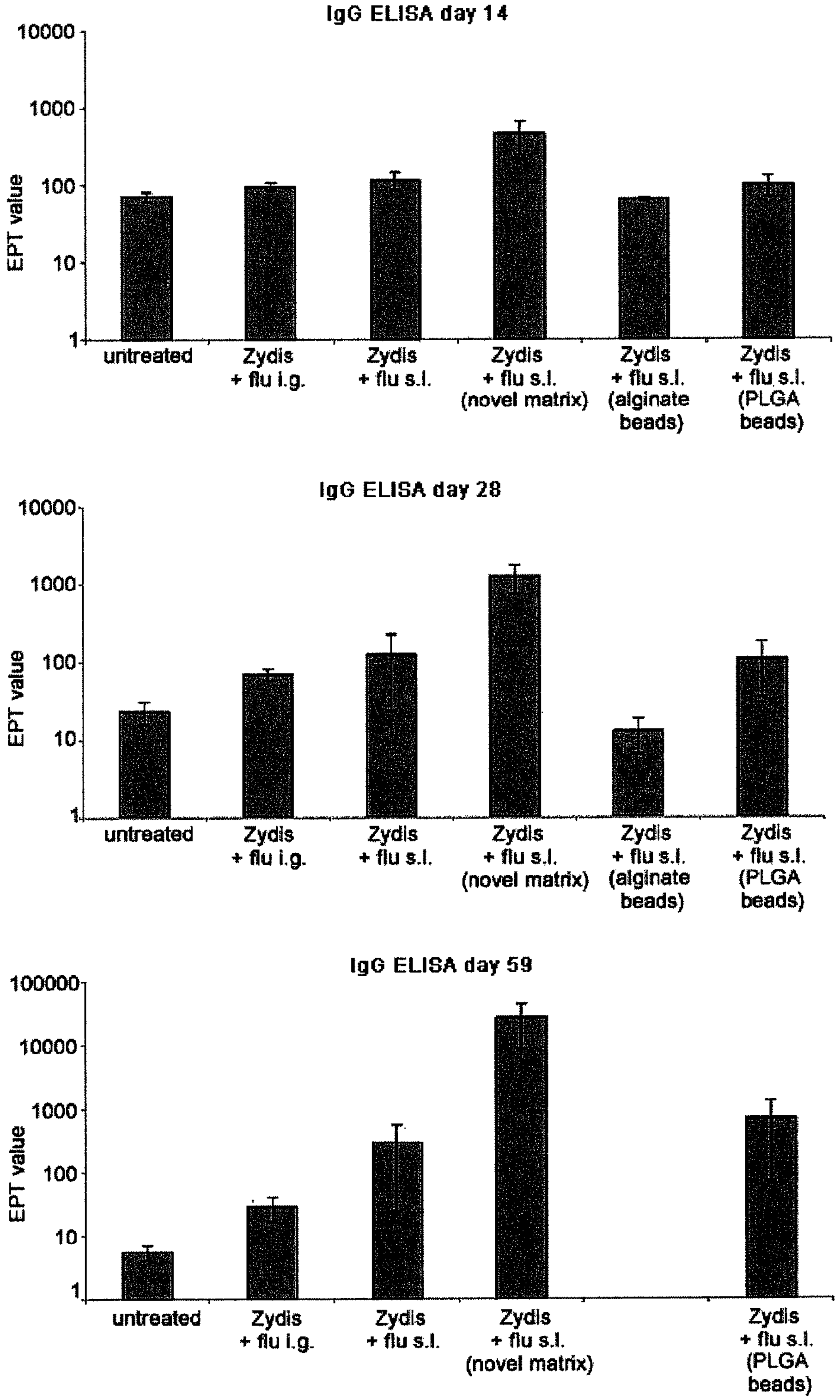
FIG. 1 shows the group mean end point titres (EPT)+/−SEM (n=8 per group) at 14, 28 and 59 days for a fast-dissolving oral solid vaccine dosage form of the present invention as compared with formulations of the comparative examples and as compared with untreated mice.

The present invention solves problems in the art by developing an FDDF that delivers an oral vaccine to invoke an improved immunogenic response for protection against infections caused by bacteria, viruses or other microorganisms. The inventors discovered that an FDDF of the present invention, employing a starch as an immune response potentiating matrix forming agent, optionally, along with at least one additional matrix forming agent, for delivery of vaccines better stimulates immunity to infections in the human body. The invention provides for the surprising results achieved in immune response when using a formulation containing a starch to make an FDDF, wherein the starch potentiates an immune response providing both a systemic humoral antibody and cell mediated response. Therefore, it can be effective against a range of antigens.

A novel and surprising aspect of the present invention is that the starch based formulations circumvent obstacles to the oral delivery of vaccine antigens as described above. The ability to overcome the natural processes that act as a barrier to the generation of an effective immune response following oral vaccine delivery results from the unique attributes of the formulations disclosed herein. The starch based fast dissolving formulations' being of a microparticulate nature facilitate uptake of the antigen within the oral cavity (preferably via sublingual or buccal administration), thereby avoiding the degradation mechanisms of the GIT. This uptake mechanism invokes both a humoral antibody and mucosal response without the need for potent adjuvants.

The immune response profile achieved shows that the invention is applicable to any sub-unit vaccine, protein conjugate and toxoid vaccines, rendering it effective against all infective agents, i.e., antigen preparations from virus, bacterial (whole or partial fragments or extracts of bacterial cells or viral particles), or parasitic derivation, such as a protozoan or worm, which cause disease, or combinations thereof.

The first embodiment is directed a fast-dissolving oral solid vaccine dosage form comprising: (a) an immunogenic amount of an antigenic preparation; and (b) at least one immune response potentiating matrix forming agent, wherein the at least one immune response potentiating matrix forming agent is a starch.

Herein, the phrases "fast-dissolving", "fast-dispersing", and "rapidly disintegrating" may be used interchangeably. For purposes of the present invention, "fast-dissolving" refers to the capability of the inventive solid dosage form to preferably disintegrate within 60 seconds (one minute) of placement in the oral cavity and/or contact with saliva. In more preferred embodiments, the dosage form disintegrates within 30 seconds, in further preferred embodiments, within 10 seconds, and in most preferred embodiments, within 5 seconds. As used herein, "oral" and "oral dosage form" refer to a pharmaceutical formulation which is administered by placement in the oral cavity of a human or animal. "Oral cavity", as used herein, refers to all spaces inside the mouth and throat of a human or animal, including on or under the tongue (sublingual) or in the buccal or pharyngeal region.

An "antigenic preparation" as used herein is a formulation incorporating soluble or particulate antigens, which can be peptides, proteins, polysaccharides, whole or partial fragments or extracts of bacterial cells or viral particles, or can be derived from a parasite, such as a protozoan or worm, which cause disease, or combinations thereof. Any antigen known in the art is suitable for use in the present invention, including those commercially available, or made by purification of preparations of a pathogen, recombinantly expressed in harmless vectors, or produced synthetically by standard manufacture. Methods for generating suitable antigens and antigen preparations for incorporation into an FDDF are known in the art, and any of the known methods may be used in the present invention.

The antigenic preparation is included in the fast-dissolving oral solid vaccine dosage form of the present invention in an amount, which is sufficient to render it immunogenic when provided in the form of the FDDF. The "immunogenic amount" is defined as the amount appropriate to provoke a desired immune response. For influenza, the immunogenic amount of the antigenic preparation is preferably about 1 μg to about 1 mg. One skilled in the art can readily determine the immunogenic amount for a given disease or infection based on, among other factors, age and weight of the patient to whom the FDDF will be administered.

The fast-dissolving solid oral vaccine dosage form of the present invention can be used to deliver vaccines which prevent or reduce the symptoms (i.e., stimulate immunity by inducing the creation of antibodies and T lymphocytes) of a wide variety of diseases. To that end, the antigenic preparation of the present invention can contain antigens useful in providing protection against the following representative list of diseases which is not exhaustive: influenza, tuberculosis, meningitis, hepatitis, whooping cough, polio, tetanus, diphtheria, malaria, cholera, herpes, typhoid, HIV, AIDS, measles, lyme disease, travellers' diarrhea, hepatitis A, B and C, otitis media, dengue fever, rabies, parainfluenza, rubella, yellow fever, dysentery, legionnaires disease, toxoplasmosis, q-fever, hemorrhagic fever, Argentina hemorrhagic fever, caries, chagas disease, urinary tract infection caused by *E. coli*, pneumoccoccal disease, mumps, chikungunya, and combinations thereof. In addition, the antigenic preparation of the present invention may contain antigens useful in providing protection against disease caused by the following, non-exhaustive list of causative organisms: *Vibrio* species, *Salmonella* species, *Bordetella* species, *Haemophilus* species, Toxoplasmosis gondii, Cytomegalovirus, *Chlamydia* species, Streptococcal species, Norwalk Virus, *Escherischia coli, Helicobacter pylori*, Rotavirus, *Neisseria gonorrhae, Neisseria meningiditis*, Adenovirus, Epstein Barr virus, Japanese Encephalitis Virus, Pneumocystis carini, Herpes simplex, Clostridia species, Respiratory Syncytial Virus, *Klebsiella* species, *Shigella* species, *Pseudomonas aeruginosa*, Parvovirus, *Camylobacter* species, *Rickettsia* species, Varicella zoster, *Yersinia* species, Ross River Virus, J.C. Virus, *Rhodococcus equi, Moraxella catarrhalis, Borrelia burgdorferi, Pasteurella haemolytica*, and combinations thereof.

Veterinary applications of the present invention are also contemplated. Accordingly, the antigenic preparation of the present invention may contain antigens useful in providing protection against the following representative list of veterinary diseases: coccidiosis, Newcastle disease, enzootic pneumonia, feline leukemia, atrophic rhinitis, erysipelas, foot and mouth disease, swine, pneumonia, and other disease conditions and other infections affecting companion and farm animals, and combinations thereof.

The fast-dissolving oral solid vaccine dosage form of the first embodiment of the invention comprises at least one immune response potentiating matrix forming agent, wherein the at least one immune response potentiating matrix forming agent is a starch. As used herein, starch refers not only to native starches but also to a wide variety of starch-related products and, more generally, to any material which provides the same functionality as starch in the fast-dissolving oral solid vaccine dosage form of the present invention. Preferably, the starch is selected from native starch, modified starch and combinations thereof. Preferably, the modified starch is selected from a group consisting of pre-gelatinized starch, substituted starch, cross-linked starch, degraded starch, and combinations thereof. Exemplary native starches include, without limitation, potato, wheat, corn (maize), cassava (tapioca), barley, arrowroot, rice, sag, sorghum, oat, millet, and combinations thereof. Exemplary modified starches further include, without limitation, starches prepared from native starches but physically, enzymatically, chemically or otherwise treated such as hydroxyalkyl starches (e.g., hydroxypropyl starch), carboxyalkyl starches (e.g., carboxymethyl starch), quarternary ammonium cationic starches (e.g., starch betainate), starch esters (e.g., acylated distarch phosphate, starch sodium octenylsuccinate, acetylated distarch adipate, starch nitrate, starch sulphate, monostarch phosphate, distarch phosphate, starch carbate, etc.). Exemplary degraded starches, prepared by physically, thermally, chemically, enzymatically or otherwise treating starch, include without limitation, dextrin, maltodextrin, pullulan, glucose, cyclodextrin, and combinations thereof.

The amount of starch in a solution or suspension subsequently frozen to form the fast-dissolving oral solid vaccine dosage form ranges preferably from about 1% to about 12%, more preferably from about 2% to about 10%, and most preferably from about 2% to about 8% by weight. The solution or suspension of antigen can be dispensed in any quantity to be frozen and freeze dried to provide the final quantity in the dried product. For example, if 30 mg of a 2% solution is dispensed and dried then the dried tablet will contain 0.6 mg of starch whereas if 1 g of the same solution is dispensed and dried then the dried tablet will contain 20 mg of starch. This provides the necessary flexibility for dosing to different patient populations. Preferably, the amount of starch present in the fast-dissolving oral solid vaccine dosage form ranges from about 2% to about 90%, more preferably from about 5% to about 80%, and most preferably from about 7% to about 75% by weight.

Without being limited to one theory, it is believed that because starch is made up of multiparticulates of granular structure, this potentiates the sampling, or uptake, of the antigens onto the granular surface and when the starch is absorbed into the blood stream, the antigens are absorbed with it. Therefore, it is believed that starch has a functionality beyond acting as a matrix forming agent in the present invention, e.g., it acts as an immune response potentiating matrix forming agent. In addition to improving the delivery of antigens to the human body, it is believed that starch assists in and improves the absorption of proteins and peptides in the human body in general.

As used herein, "immune response potentiating" means that the matrix forming agent is responsible, at least in part, for the type or degree of immune response achieved by the fast-dissolving oral solid vaccine dosage form of the present invention.

In a preferred embodiment, the fast-dissolving oral solid vaccine dosage form further comprises at least one additional matrix forming agent. One or more additional matrix forming agents may be incorporated into the solution or suspension prior to freezing to form the fast-dissolving oral solid vaccine dosage form during manufacture. Any conventional matrix forming agent is suitable for use in the present invention as an additional matrix forming agent. Suitable additional matrix forming agents include, without limitation, materials derived from animal or vegetable proteins, such as the gelatins, dextrins and soy, wheat and psyllium seed proteins; gums; polysaccharides; alginates; carboxymethylcelluloses; carrageenans; dextrans; pectins; synthetic polymers such as polyvinylpyrrolidone; polypeptide/protein or polysaccharide complexes such as gelatin-acacia complexes; sugars such as mannitol, dextrose, lactose, galactose and trehalose; cyclic sugars such as cyclodextrin; inorganic salts such as sodium phosphate, sodium chloride and aluminum silicates; and amino acids having from 2 to 12 carbon atoms such as a glycine, L-alanine, L-aspartic acid, L-glutamic acid, L-hydroxyproline, L-isoleucine, L-leucine and L-phenylalanine, or combinations thereof. The amount of the at least one additional matrix forming agent present in the fast-dissolving oral solid vaccine dosage form may range preferably from about 10% to about 98%, more preferably from about 20% to about 95%, and most preferably from about 25% to about 93% by weight. The amount of the at least one additional matrix forming agent present in a solution or suspension subsequently frozen to form the fast-dissolving oral solid vaccine dosage form ranges preferably from about 0.01% to about 45%, more preferably from about 0.01% to about 33%, and most preferably from about 0.01% to about 21% by weight.

In addition to forming the matrix, the matrix forming agent may aid in maintaining the dispersion of any antigenic preparation with the solution or suspension. This is especially helpful in the case of antigenic preparations that are not sufficiently soluble in water and must, therefore, be suspended rather than dissolved.

In a preferred embodiment, the at least one additional matrix forming agent is mannitol. In yet another preferred embodiment, the at least one additional matrix forming agent is gelatin. In still another preferred embodiment, the at least one additional matrix forming agent comprises mannitol and gelatin, in combination with starch as the at least one immune response potentiating matrix forming agent.

When present, the amount of mannitol in the fast-dissolving oral solid vaccine dosage form ranges preferably from about 2% to about 90%, more preferably from about 5% to about 80%, and most preferably from about 7% to about 65% by weight. When present, the amount of mannitol in a solution or suspension subsequently frozen to form the fast-dissolving oral solid vaccine dosage form ranges preferably from about 1% to about 15%, more preferably from about 2% to about 10%, and most preferably from about 2% to about 5% by weight. When present, the amount of gelatin in the fast-dissolving oral solid vaccine dosage form ranges preferably from about 2% to about 85%, more preferably from about 2.5% to about 65%, and most preferably from about 3% to about 55% by weight. When present, the amount of gelatin in a solution or suspension subsequently frozen to form the fast-dissolving oral solid vaccine dosage form ranges preferably from about 1% to about 10%, more preferably from about 1% to about 7%, and most preferably from about 1% to about 4% by weight.

In a preferred embodiment of the invention, in the fast-dissolving oral solid vaccine dosage form, gelatin is present in an amount of about 3% to about 55%; mannitol is present in an amount of about 7% to about 65%; and a starch is present in an amount of about 7% to about 75% by weight. In a preferred embodiment of the invention, in a solution or suspension subsequently frozen to form the fast-dissolving oral solid vaccine dosage form, gelatin is present in an amount of about 1% to about 4%; mannitol is present in an amount of about 2% to about 5%; and a starch is present in an amount of about 2% to about 8% by weight.

In another preferred embodiment, the at least one additional matrix forming agent is a gum such as, but not limited to, acacia, guar, agar, xanthan, gellan, carageenan, curdlan, konjac, locust bean, welan, gum tragacanth, gum arabic, gum karaya, gum ghatti, pectins, dextran, glucomannan, and alginates, or combinations thereof. When present, the gum in the fast-dissolving oral solid vaccine dosage form ranges preferably in an amount from about 0.01% to about 80% by weight. When present, the gum in a solution or suspension subsequently frozen to form the fast-dissolving oral solid vaccine dosage form ranges preferably in an amount ranging from about 0.01% to about 10% by weight. In a more preferred embodiment, the at least one additional matrix forming agent is xanthan gum. When present, the xanthan gum in the fast-dissolving oral solid vaccine dosage form ranges preferably in an amount from about 0.01% to about 80% by weight. When present, the xanthan gum in a solution or suspension subsequently frozen to form the fast-dissolving oral solid vaccine dosage form ranges preferably in an amount ranging from about 0.01% to about 10% by weight. When xanthan gum is added to the solution or suspension, the immune potentiating response with respect to IL-6 and TNFalpha may be increased over solutions or suspensions not containing xanthan gum.

In a preferred embodiment, the at least one additional matrix forming agent comprises mannitol, gelatin and xanthan gum. In a further preferred embodiment of the invention, in the fast-dissolving oral solid vaccine dosage form, gelatin is present in an amount of about 3% to about 55%; mannitol is present in an amount of about 7% to about 65%; a starch is present in an amount of about 7% to about 75%; and xanthan gum is present in an amount of about 0.01% to about 80% by weight. In a preferred embodiment of the invention, in a solution or suspension subsequently frozen to form the fast-dissolving oral solid vaccine dosage form, gelatin is present in an amount of about 1% to about 4%; mannitol is present in an amount of about 2% to about 5%; a starch is present in an amount of about 2% to about 8% by weight; and xanthan gum is present in an amount of about 0.01% to about 10% by weight.

In another embodiment of the present invention, the fast-dissolving oral solid vaccine dosage form further comprises a surfactant. Any surfactant known in the art is suitable for use in the present invention, including non-ionic, anionic and cationic surfactants. Examples of non-ionic surfactants that may be used in the present invention include, but are not limited to, polyethylene alkyl ethers, polyoxyethylene alkyl ethers, polyoxyethylene sorbitan fatty acid esters (e.g., Tweens), polyoxyethylene stearates, sorbitan fatty acid esters (e.g., Spans), and polyoxyethylene-polyoxypropylene co-polymers (e.g., poloxamers). Examples of anionic surfactants that may be used in the present invention include, but are not limited to, sodium lauryl sulphate, docusate sodium, and glycerol monooelate. Examples of cationic surfactants that may be used in the present invention include, but are not limited to, benzalkonium chloride, cetrimide, and cetylpyridinium chloride. Preferably, the surfactant is selected from the group consisting of Tween 80 (polysorbate 80), poloxamer, and combinations thereof. When present, the surfactant in the fast-dissolving oral solid vaccine dosage form ranges preferably in an amount from about 0.01% to about 80% by weight. When present, the surfactant in a solution or suspension subsequently frozen to form the fast-dissolving oral solid vaccine dosage form ranges preferably in an amount from about 0.01% to about 10% by weight. When a surfactant is added to the solution or suspension, the immune potentiating response may be increased over solutions or suspensions not containing a surfactant.

In a preferred embodiment of the present invention, the at least one additional matrix forming agent comprises mannitol and gelatin and the fast-dissolving oral solid vaccine dosage form further comprises a surfactant. In a further preferred embodiment of the invention, in the fast-dissolving oral solid vaccine dosage form, gelatin is present in an amount of about 3% to about 55%; mannitol is present in an amount of about 7% to about 65%; a starch is present in an amount of about 7% to about 75%; and a surfactant is present in an amount of about 0.01% to about 80%. In a preferred embodiment of the invention, in a solution or suspension subsequently frozen to form the fast-dissolving oral solid vaccine dosage form, gelatin is present in an amount of about 1% to about 4%; mannitol is present in an amount of about 2% to about 5%; a starch is present in an amount of about 2% to about 8% by weight; and a surfactant is present in an amount of about 0.01% to about 10% by weight.

The dosage form of the invention optionally further comprises an adjuvant, which is useful in boosting an immune response to dead or inactivated vaccines, resulting in enhanced production of antibodies and enhanced immunological memory. To be most effective, the immune response is associated with the generation of a memory response that provides long lasting protection from the specific disease. Once exposed, the immune system "remembers" the antigen and the immune response initiated to inactivate the antigen. The effectiveness of an adjuvant to enhance an immune response can be independent from the antigen with which it is being combined. Suitable adjuvants include, but are not limited to: non-toxic bacterial fragments, cholera toxin (and detoxified forms and fractions thereof), chitosan, heat-labile toxin of *E. coli* (and detoxified forms and fractions thereof), lactide/glycolide homo.+−.and copolymers (PLA/GA), polyanhydride, e.g., trimellitylimido-L-tyrosine, DEAE-dextran, saponins complexed to membrane protein antigens (immune stimulating complexes—ISCOMS), bacterial products such as lipopolysaccharide (LPS) and muramyl dipeptide, (MDP), liposomes, cochleates, proteinoids, cytokines (interleukins, interferons), genetically engineered live microbial vectors, non-infectious pertussis mutant toxin, neurimidase/galactose oxidase, and attenuated bacterial and viral toxins derived from mutant strains, and combinations thereof. A suitable amount of an adjuvant can be readily determined by one of ordinary skill in the art.

The dosage form of the present invention promotes delivery of a vaccine to a target site, and, in certain embodiments, a mucoadhesive system can be designed to maintain the vaccine in contact with the target mucosal lymphoid tissues in the oral cavity and to increase the residence time of the vaccine element at these potential surfaces for absorption. As a product for oral ingestion, from which the vaccine is quickly released once the product is taken, high concentrations of vaccine can thus be quickly delivered to the desired target sites.

Some fast-dissolving solid dosage forms are inherently mucoadhesive. Nevertheless, a mucoadhesive may optionally be added to the fast-dissolving dosage form of the present invention, which can increase the residency of the antigen in contact with the mucosal tissue in the oral cavity. Suitable mucoadhesives that can be used in the present invention include, but are not limited to, those described in European Patent Application No. 92109080.9 and include: polyacrylic polymers such as carbomer and carbomer derivatives (e.g., Polycarbophil™, Carbopol™, and the like); cellulose derivatives such as hydroxypropylmethylcellulose (HPMC), hydroxyethylcellulose (HEC), hydroxypropylcellulose (HPC) and sodium carboxymethylcellulose (NaCPC); and natural polymers such as gelatin, sodium alginate, and pectin. Suitable commercial sources for representative mucoadhesive (bioadhesive) polymers include, but are not limited to, Carbopol™ acrylic copolymer (available from BF Goodrich Chemical Co., Cleveland, Ohio); hydroxypropylmethylcellulose (HPMC) (available from Dow Chemical, Midland, Mich.); HEC (Natrosol) (available from Hercules Inc., Wilmington, Del.); HPC (Klucel™) (available from Dow Chemical Co., Midland, Mich.); MaCMC (available from Hercules, Inc., Wilmington, Del.); gelatin (available from Deamo Chemical Corp., Elmford, N.Y.); sodium alginate (available from Edward Mandell Co., Inc., Carmel, N.Y.); pectin (available from BDH Chemicals Ltd., Poole, Dorset, UK); Polycarbophil™ (available from BF Goodrich Chemical Co., Cleveland, Ohio). A suitable amount of a mucoadhesive can be readily determined by one of ordinary skill in the art.

The fast-dissolving oral solid vaccine dosage form of the present invention may also contain other optional components such as preservatives, antioxidants, viscosity enhancers, coloring agents, flavoring agents, pH modifiers, sweeteners, taste-masking agents and combinations thereof. Suitable coloring agents include, without limitation, red, black and yellow iron oxides and FD&C dyes such as FD&C blue No. 2 and FD&C red No. 40 available from Ellis & Everard. Suitable flavoring agents include, without limitation, mint, raspberry, licorice, orange, lemon, grapefruit, caramel, vanilla, cherry and grape flavors, and combinations of these. Suitable pH modifiers include, without limitation, citric acid, tartaric acid, phosphoric acid, hydrochloric acid, maleic acid, sodium hydroxide, sodium carbonate and tris-buffer. Suitable sweeteners include, without limitation, aspartame, sucrose, sucralose, acesulfame K and thaumatin. Suitable taste-masking agents include, without limitation, sodium bicarbonate, and cyclodextrin inclusion compounds. One of ordinary skill in the art can readily determine suitable amounts of these optional ingredients for inclusion in the fast-dissolving oral solid vaccine dosage form of the present invention.

In a certain embodiment of the invention, the fast-dissolving oral solid vaccine dosage form can optionally include microspheres which can be biodegradable. The microsphere material itself may function as an adjuvant or may be used in conjunction with other adjuvants. The antigenic preparation may be absorbed or incorporated onto or into microspheres, thereby forming a microsphere-antigenic complex. Thus, the antigenic preparation is available for absorption into the lymphoid tissue effectively as soon as the tissue contacts the microsphere-antigen preparation complex.

Suitable microsphere materials that can be used with the invention include biodegradable polymeric materials. Particularly suitable are hydrophobic materials such as poly (lactic acid) and poly(lactide-co-glycide) polymers, and latex copolymers. These polymeric materials also confer resistance to enzymatic and hydrolytic digestion until their absorption into lymphoid tissue, where the liberated antigen can exert its immunogenic effect. Preferred polymeric materials are hydrophobic materials which enhance absorption into the target tissues. In preferred embodiments, the microsphere is sodium alginate or poly(lactide-co-glycide) (PLGA).

When the fast-dissolving oral solid vaccine dosage form of the first embodiment is administered to the oral cavity of a patient (human or animal) in need of disease protection, an immune response is induced. An immune response includes the production of antibodies specific to the pathogen from which the antigen within the dosage form was derived, the generation of suitable T cell antibody and, in some cases, the production of cytotoxic T lymphocytes (CTL). The immune response may also include the generation of a memory response that provides long-lasting protection from the specific disease.

In the present invention, placement of the fast-dissolving oral solid vaccine dosage form is preferably on or under the tongue (sublingual) or in the buccal or pharyngeal region.

The fast-dissolving oral solid vaccine dosage forms of the present invention can be taken without water and disperse in very small volumes of saliva. This increases the coating of mucosal tissues containing the tonsillar associated lymphoid tissue and increases the residence time of antigens within these tissues. Fast-dissolving oral solid dosage forms are known to rapidly disperse and coat the mucosal surfaces in the mouth and pharynx, where the mucosal associated lymphoid tissues are localized. In this respect, reference is directed to a paper by Wilson et al., International Journal of Pharmaceutics, 40 (1997), pages 119-123, the text of which is incorporated herein by reference. Accordingly, fast-dissolving oral solid dosage forms improve the targeting of vaccines to susceptible lymphoid tissues in the mouth, particularly under the tongue, and the pharynx. Consequently, the concentration of vaccine making contact with these tissues, e.g., susceptible lymphoid tissue in the buccopharyngeal and sublingual areas, increases when delivered via FDDF.

Any known method of manufacture of fast-dissolving dosage forms can be used in accordance with this invention. Preferably the fast-dissolving oral solid vaccine dosage forms of the present invention are freeze-dried. A preferred fast-dissolving dosage form for use with the invention is that described in U.K. Patent No. 1,548,022, which is directed to a solid fast-dissolving solid oral dosage form comprising a network of the active ingredient and a water-soluble or water-dispersible carrier which is inert toward the active ingredient, the network having been obtained by subliming solvent from a composition comprising the active ingredient and a solution of the carrier in a solvent. U.K. Patent No. 1,548,022 fails to disclose the use of a starch in a freeze-dried FDDF, but the method therein can be readily adapted to make the fast-dissolving oral solid vaccine dosage forms of the present invention.

The fast-dissolving oral solid vaccine dosage form is typically a white, round tablet formulated to rapidly disintegrate in the mouth. However, the color may vary depending on the materials used therein or the addition of colorants. The tablet size is generally about 5 mm to about 25 mm and shaped according to the size and shape of the blister cavity into which it will be placed during manufacture and/or storage. The tablet comprises a highly porous network which assists disintegration typically within 60 seconds, more preferably within 30 seconds, still more preferably within 10 seconds, and most preferably within 5 seconds, after being placed in the oral cavity. The tablet is physically robust in order to withstand handling and removal from the blister packaging without breaking.

In a second embodiment, the fast-dissolving oral solid vaccine dosage form comprises: (a) an immunogenic amount of inactivated influenza virus; and (b) at least one immune response potentiating matrix forming agent, wherein the at least one immune response potentiating matrix forming agent is a starch.

Any strain of influenza virus is suitable for use in the present invention. In the manufacture of vaccines for influenza, international organizations, such as the World Health Organization, monitor disease causing strains and annually provide specific information on the most important strains for which vaccination is required. Because of the continuing mutation of key antigens on the surface of the influenza virus, new strains are continually monitored and new vaccines manufactured. Samples of the identified influenza strains are made available to vaccine manufacturers who use them for the preparation of vaccines. Viruses are generally prepared for use in a vaccine, i.e., an antigenic preparation, according to known standard procedures. Inactivated influenza virus can be included in the fast-dissolving oral solid vaccine dosage form of the invention in an immunogenic amount. Typically, the amount of virus to be added is defined from immunogenicity studies in animals where the levels of functional antibodies as defined in assays, such as the Haemagglutination Inhibition (HAI) assay, reach a desired level as agreed upon by vaccine regulators.

The details noted above regarding immunogenic amount, starch, matrix forming agents, surfactants, microspheres, adjuvant, mucoadhesive, etc. are the same for the second embodiment of the invention as for the first embodiment of the invention.

When the fast-dissolving oral solid vaccine dosage form of the second embodiment is administered to the oral cavity of a patient (human or animal) in need of protection from influenza, an influenza specific antibody response is induced. This antibody response neutralizes the ability of the virus to infect mammalian cells, as measured by the HAI or Virus Neutralization Test (VNT), which assesses the functional ability of the antibody response. Other desired aspects of the anti-influenza immune response include the generation of memory B and T cell responses and the presence of CTL, which is able to kill cells infected by the virus. Most vaccines are currently evaluated solely on their ability to stimulate an antibody response. However, the ability to produce vaccines capable of conferring cross-influenza strain protective immunity may be achieved by enhancing the ability of new vaccines to generate CTL. Placement of the fast-dissolving oral solid vaccine dosage form is preferably on or under the tongue (sublingual) or in the buccal or pharyngeal region.

The third embodiment of the present invention is directed to a method of inducing an immune response in a patient, said method comprising the step of: placing the fast-dissolving oral solid vaccine dosage form of the first embodiment of the invention in the oral cavity of a person in need of the immune response. Preferably, placement in the oral cavity is placement on or under the tongue (sublingual) or in the buccal or pharyngeal region.

In preferred embodiments of the invention, the fast-dissolving oral solid vaccine dosage form is administered to induce an immune response greater than a negative control and greater than administration of an FDDF without the inclusion of a starch as an immune response potentiating matrix forming agent. "Negative control" as defined herein is an animal used in experiments which is untreated with the inactivated virus and uninfected by the virus.

The fourth embodiment of the present invention is directed to a method of inducing an influenza specific IgG response in a patient, said method comprising the step of: placing the fast-dissolving oral solid vaccine dosage form of the second embodiment of the invention in the oral cavity of a person in need of the immune response. Preferably, placement in the oral cavity is placement on or under the tongue (sublingual) or in the buccal or pharyngeal region.

The present invention is not limited to any specific vaccine, but to solving the problems of oral delivery of vaccines. The following examples will illustrate the practice of the present invention in some of the preferred embodiments. Other embodiments within the scope of the claims will be apparent to one skilled in the art.

Example 1

An FDDF of the kind known in the art as described in Seager, H., "Drug-Delivery Products and Zydis Fast Dissolving Dosage Form," *J. Pharm. Pharmacol*, vol. 50, p. 375-382 (1998) was prepared, but with gelatin, mannitol and starch. The novel matrix formulation was prepared by combining 1.5% (375 mg) Bovine limed hide gelatin, 2.5% (625 mg) hydroxypropyl starch, 3.0% (750 mg) mannitol and 25 ml water and heating the mixture to 75° C. for 15 minutes. The solution was covered during heating to minimize evaporation. The solution was subsequently cooled to ambient temperature, e.g., 20-25° C., in a chilled water bath. 5.5 μl of stock influenza (A/Panama/2007/99 H3N2) solution was added to 24.5 μl of the novel matrix formulation so that each tablet contained 1 μg of influenza. After addition of the stock influenza, final concentrations of the matrix forming agents in the formulation were as follows: 2.0% starch (w/v), 2.4% mannitol (w/v) and 1.2% gelatin (w/v). The formulation was then dosed into blister pockets using a semi-automatic Hamilton dosing pump dispensing 30 mg per dose. The dosed formulations were then rapidly frozen by being placed in a liquid nitrogen chamber for 5 minutes. The frozen formulations were subsequently freeze-dried using an Edwards, Modulyo 4K freeze drier attached to an Edwards RV5 pump. First, the freeze-drier was activated for a period of 15 minutes to pre-cool the system to −45° C. The frozen formulations were then transferred immediately onto the rack within a chamber of the freeze-drier. The lid was placed on the chamber, and the vacuum pump was turned on to ensure that the drainage valve was shut. The freeze-drier was allowed to run overnight to completely freeze-dry the samples. Once dry, the vacuum pump and condenser were turned off and the drainage tap turned slowly to allow air into the system. The filled fully-frozen blister packs were then removed and placed in foil sachets and sealed in a glass jar containing desiccant and stored at 4° C. until use.

The freeze-dried tablets were visually inspected; no major defects were found. Tablets were all intact and looked normal other than being slightly raised. The tablets disintegrated instantly, within ten seconds, on being placed in purified water at 37° C.

The resulting tablets were administered sublingually to mice, and blood samples were subsequently tested on days 14, 28 and 59. Subclass ELISAs were performed to assess the levels of Flu-specific IgG1 and IgG2a in serum samples collected from the treated animals. Samples were diluted to give a top concentration of 1 in 40. A serial 2-fold dilution of samples was then performed in phosphate buffered saline with bovine serum albumin (PBS/BSA) (1%) across the 96 well plate. Horeseradish peroxidase (HRP)-conjugated detection antibodies, goat anti-mouse IgG1 and IgG2a (Fc): HRP conjugate (both from AbD Serotec) were diluted 1 in 1000 in PBS/BSA. Serum from animals which were untreated and uninfected were included as a negative control. The results are shown in FIG. 1 below as "Zydis+flu s.l. (novel matrix)".

Comparative Example 1

An FDDF was prepared according to the generally known preparation of a Zydis® tablet. The Zydis® tablet was prepared by combining 200 mg of gelatin with 3.3 ml of water and heating the mixture to 60° C. for 30 minutes. The solution was covered during heating to minimize evaporation. The solution was subsequently cooled to about 25° C. in a chilled water bath. Following this, 150 mg mannitol was added while stirring. A stock solution of influenza antigen A/Panama/2007/99 H3N2 was added to bring the volume to 5 ml so that each tablet contained 1 μg of influenza. The final concentration of the matrix forming agents after the addition of the influenza was 4% gelatin (w/v) and 3% mannitol (w/v). The formulation was processed under the same conditions as Example 1, i.e., dissolving, cooling, freezing, freeze-drying. The freeze-dried tablets were inspected in the same manner as in Example 1. The freeze-dried tablets were inspected for surface defects; no major defects were found and the tablets were intact. A dispersion test (by placing a tablet in 100 μl purified water at 37° C.) was carried out on the Zydis® tablets and they dissolved in less than 10 seconds.

Two batches were made according to this process. The resulting tablets from the first batch were administered sublingually to mice, while 10 tablets from the second batch were dissolved in 2 ml of water warmed to 37° C. and 200 μl was administered per animal intragastrically (i.g.). Blood samples were subsequently tested from mice in each group on days 14, 28 and 59. Subclass ELISAs were performed to assess the levels of Flu-specific IgG1 and IgG2a in serum samples collected from the treated animals. Samples were diluted to give a top concentration of 1 in 40. A serial 2-fold dilution of samples was then performed in PBS/BSA (1%) across the 96 well plate. HRP-conjugated detection antibodies, goat anti-mouse IgG1 and IgG2a (Fc):HRP conjugate (both from AbD Serotec) were diluted 1 in 1000 in PBS/BSA. Serum from animals which were untreated and uninfected were included as a negative control. The results are shown in FIG. 1 below as "Zydis+flu s.l." and as "Zydis+flu i.g.," respectively.

Comparative Example 2

An FDDF was prepared according to Comparative Example 1, except prior to dosing into blister pockets, sodium alginate microencapsulated A/Panama/2007/99 H3N2 influenza virus was added to the formulation so that each tablet contained 1 μg of influenza. To achieve that final amount, 3 microencapsulated influenza beads were added per tablet. The solution was subsequently processed under the same conditions as Example 1, i.e., dissolving, cooling, freezing, freeze-drying. The freeze-dried tablets were inspected in the same manner as in Example 1.

The freeze-dried tablets were inspected for surface defects; no major defects were found. A dispersion test (by placing a tablet in 100 μl purified water at 37° C.) was carried out on the tablets, and they dissolved in less than 10 seconds.

The resulting tablets were administered sublingually to mice, and blood samples were subsequently tested on days 14 and 28. Subclass ELISAs were performed to assess the levels of Flu-specific IgG1 and IgG2a in serum samples collected from the treated animals. Samples were diluted to give a top concentration of 1 in 40. A serial 2-fold dilution of samples was then performed in PBS/BSA (1%) across the 96 well plate. HRP-conjugated detection antibodies, goat anti-mouse IgG1 and IgG2a (Fc):HRP conjugate (both from AbD Serotec) were diluted 1 in 1000 in PBS/BSA. Serum from animals which were untreated and uninfected were included as a negative control. The results are shown in FIG. 1 below as “Zydis+flu s.l. (alginate beads)”.

Comparative Example 3

An FDDF was prepared according to Comparative Example 1, except prior to dosing into blister pockets, PLGA microencapsulated A/Panama/2007/99 H3N2 influenza virus was added to the formulation so that each tablet contained 1 μg of influenza. To achieve that final amount, a total of 10 μl of PLGA beads was added to 20 μl of FDDF mixture to achieve an amount of 10 μl microencapsulated influenza beads per tablet. The solution was subsequently processed under the same conditions as Example 2, i.e., dissolving, cooling, freezing, freeze-drying. The freeze-dried tablets were inspected in the same manner as in Example 1.

The freeze-dried tablets were inspected for surface defects; no major defects were found on the FDDFs prepared. A dispersion test (by placing a tablet in 100 μl purified water at 37° C.) was carried out on the tablets, and they dissolved in 10 seconds.

The resulting tablets were administered sublingually to mice, and blood samples were subsequently tested on days 14, 28 and 59. Subclass ELISAs were performed to assess the levels of Flu-specific IgG1 and IgG2a in serum samples collected from the treated animals. Samples were diluted to give a top concentration of 1 in 40. A serial 2-fold dilution of samples was then performed in PBS/BSA (1%) across the 96 well plate. HRP-conjugated detection antibodies, goat anti-mouse IgG1 and IgG2a (Fc):HRP conjugate (both from AbD Serotec) were diluted 1 in 1000 in PBS/BSA. Serum from animals which were untreated and uninfected were included as a negative control. The results are shown in FIG. 1 below as “Zydis+flu s.l. (PLGA beads)”.

Example 2

As demonstrated by the examples above, the Zydis® formulation is an effective means of stimulating systemic antibody responses to antigens (Ag) following sub-lingual delivery. The profile of the immune response obtained was dependent on the Zydis® formulation and included high response of neutralizing antibodies. This is important in neutralizing extracellular viral/bacterial toxins and antigens present in the systemic circulation. The formulation of Example 1 was also able to drive the expansion of antigen-specific cytotoxic T cell (CTL), which is an important cell mediated immune response to neutralize intracellular infection. Additional work was conducted to further improve the cell mediated response achieved by the formulations.

After these first studies, additional in-vitro studies were conducted using murine splenic macrophages in culture and flow cytometry to determine their levels of activation and expression of molecules that are critical in mediating T cell activation. For the in-vitro studies, lipopolysaccharide (LPS), a known potent stimulator of many of these factors, was used as a positive control. The formulations were prepared for use in the in-vitro study using murine splenic macrophages as shown in Table 1 below.

TABLE 1

| Formulation | Antigen Dose | Base Matrix Composition In Suspension (% w/w) | Base Matrix Composition In Tablet (mg/tablet) | Base Matrix Composition In Tablet (% w/w) | Rationale |
|---|---|---|---|---|---|
| 1 | 1 μg | Starch 2.0%<br>Gelatin 1.2%<br>Mannitol 2.4% | Starch 0.6 mg<br>Gelatin 0.36 mg<br>Mannitol 0.72 mg | Starch 35.7<br>Gelatin 21.4<br>Mannitol 42.9 | Control |
| 2 | 15 μg | Starch 2.0%<br>Gelatin 1.2%<br>Mannitol 2.4% | Starch 0.6 mg<br>Gelatin 0.36 mg<br>Mannitol 0.72 mg | Starch 35.7<br>Gelatin 21.4<br>Mannitol 42.9 | Increase dose of antigen |
| 3 | 1 μg | Starch 6.5%<br>Gelatin 1.2%<br>Mannitol 2.4% | Starch 1.95 mg<br>Gelatin 0.36 mg<br>Mannitol 0.72 mg | Starch 64.4<br>Gelatin 11.9<br>Mannitol 23.8 | Increase dose of starch |
| 4 | 15 μg | Starch 6.5%<br>Gelatin 1.2%<br>Mannitol 2.4% | Starch 1.95 mg<br>Gelatin 0.36 mg<br>Mannitol 0.72 mg | Starch 64.4<br>Gelatin 11.9<br>Mannitol 23.8 | Increase dose of antigen & starch |
| 5* | 15 μg | Starch 6.5%<br>Gelatin 1.2%<br>Mannitol 2.4% | Starch 1.95 mg<br>Gelatin 0.36 mg<br>Mannitol 0.72 mg | Starch 64.4<br>Gelatin 11.9<br>Mannitol 23.8 | Impact of processing |
| 6 | 15 μg | Starch 6.5%<br>Gelatin 1.2%<br>Mannitol 2.4%<br>Tween 80 0.2%<br>(polysorbate 80) 0.2% | Starch 1.95 mg<br>Gelatin 0.36 mg<br>Mannitol 0.72 mg<br>Tween 80<br>(polysorbate 80)<br>0.06 mg | Starch 63.1<br>Gelatin 11.7<br>Mannitol 23.3<br>Tween 80<br>(polysorbate 80)<br>1.9 | Addition of surfactant; for comparison to Formulation 4 |
| 7 | 15 μg | Starch 6.5%<br>Gelatin 1.2%<br>Mannitol 2.4%<br>Poloxamer 188 0.2% | Starch 1.95 mg<br>Gelatin 0.36 mg<br>Mannitol 0.72 mg<br>P188 0.06 mg | Starch 63.1<br>Gelatin 11.7<br>Mannitol 23.3<br>P188 1.9 | Addition of surfactant; for comparison to Formulation 4 |
| 8 | 15 μg | Starch 6.5%<br>Gelatin 1.2%<br>Mannitol 2.4%<br>Xanthan gum 0.05% | Starch 1.95 mg<br>Gelatin 0.36 mg<br>Mannitol 0.72 mg<br>Xanthan 0.015 mg | Starch 64.0<br>Gelatin 11.8<br>Mannitol 23.6<br>Xanthan 0.5 | Addition of complex carbohydrate; for comparison to Formulation 4 |
| 9 | 15 μg | Starch 6.5%<br>Gelatin 1.2%<br>Mannitol 2.4%<br>Lecithin 0.2% | Starch 1.95 mg<br>Gelatin 0.36 mg<br>Mannitol 0.72 mg<br>Lecithin 0.06 mg | Starch 63.1<br>Gelatin 11.7<br>Mannitol 23.3<br>Lecithin 1.9 | Addition of phospholipid; for comparison to Formulation 4 |
| 10* | 15 μg | Corn Starch 6.5%<br>Gelatin 1.2%<br>Mannitol 2.4% | Corn Starch 1.95 mg<br>Gelatin 0.36 mg<br>Mannitol 0.72 mg | Corn Starch 64.4<br>Gelatin 11.9<br>Mannitol 23.8 | High Amylose content |

TABLE 1-continued

| Formulation | Antigen Dose | Base Matrix Composition In Suspension (% w/w) | Base Matrix Composition In Tablet (mg/tablet) | Base Matrix Composition In Tablet (% w/w) | Rationale |
|---|---|---|---|---|---|
| 11* | 15 μg | Waxy Maize Starch 6.5%<br>Gelatin 1.2%<br>Mannitol 2.4% | WM Starch 1.95 mg<br>Gelatin 0.36 mg<br>Mannitol 0.72 mg | WM Starch 64.4<br>Gelatin 11.9<br>Mannitol 23.8 | High Amylopectin content |
| 12* | 15 μg | Rice Starch 6.5%<br>Gelatin 1.2%<br>Mannitol 2.4% | Rice Starch 1.95 mg<br>Gelatin 0.36 mg<br>Mannitol 0.72 mg | Rice Starch 64.4<br>Gelatin 11.9<br>Mannitol 23.8 | Small granule size |

*Processed at 50° C. All other formulations processed at 70° C.

The formulations were prepared as follows. A stock solution of flu antigen at a concentration of 3.94 mg/ml was prepared. Separately, a matrix concentrate for each formulation listed above was prepared. An appropriate quantity of flu antigen stock solution and formulation matrix concentrate was then combined to give a final volume of 500 μl final formulation solution. From this final mixed formulation solution, 30 mg aliquots were dispensed, frozen and freeze-dried to yield tablets containing either 1 μg or 15 μg of flu antigen. Table 2 summarizes this preparation.

TABLE 2

| Quantity of Matrix Solution Concentrate (μl) | Quantity of Stock Antigen Solution (μl) | Total Volume of Final Formulation Solution (μl) | Amount Dispensed to Tablet (mg) | Amount of Antigen per Tablet (μg) |
|---|---|---|---|---|
| 495.78 | 4.22 | 500 | 30 | 1 |
| 436 | 64 | 500 | 30 | 15 |

The matrix concentrate were prepared by dissolving the appropriate amount of each component in a quantity of water. An appropriate amount of the matrix concentrate, when combined with the required amount of antigen stock solution, resulted in the level of matrix component in the final mixed formulation solution in accordance with the values set forth above. For example, for Formulation 1, Table 3 demonstrates the relationship between the matrix concentrate and the percent by weight in the final formulation.

TABLE 3

| Component | Weight Dispensed for Matrix Concentrate (g) | Quantity of Matrix Solution Taken (μl) | Quantity of Antigen Solution Added (μl) | Total Volume of Final Formulation Solution (μl) | % w/w in Final Formulation Solution |
|---|---|---|---|---|---|
| Starch | 0.5 | 495.78 | 4.22 | 500 | 2 |
| Gelatin | 0.3 | | | | 1.2 |
| Mannitol | 0.6 | | | | 2.4 |
| Water | 23.29 | | | | |

Spleen cells were isolated from normal adult BALB/c mice, washed and then CD11b+ macrophages were purified by MACS separation using an LS column held within the field of a Midi/MACS™ separator. The macrophages were washed and cultured in tissue culture medium. These were set up in culture at $1.8\times10^5$ CD11b+ cells per test well. LPS was added at a final concentration of 100 ng/ml to act as a positive control. One Zydis® tablet for each of the 12 formulations was dissolved in tissue culture media and split between three replicates. Also, an unstimulated control was prepared containing neither LPS nor one of the listed formulations. After 48 hours, the cultures were harvested and supernatants removed for cytokine analysis. The cells were washed and macrophage activation assessed using flow cytometry following staining with antibodies to major histocompatibility complex (MHC) class II, CD25 and CD86.

Testing

A. In Vitro Testing

The nature of the T cell and antibody response to antigenic challenge is dictated by the state of activation and the cytokines that are produced by monocyte/macrophage/dendritic cells upon antigen contact. Adjuvants and delivery vehicles manipulate these responses in order to drive T and B cell responses of particular types. For example, stimulation of IL-12 by these cells is a major determinant associated with promoting Th1 immune responses characterized by complement fixing antibodies, phagocyte activation and CTL production. IL-4 is a major driver of Th2 responses whereas IL-6 together with TGFbeta is a major driver of mucosal IgA responses.

Various markers as an indication of the level and type of activation of the macrophages were measured. In addition, an assessment of the key cytokines they produce as an indicator of the types of immune reaction that they may promote was evaluated.

1. MHC Class II

The upregulation of class II MHC is an essential step in enhancing the presentation of antigen in order to drive the T cell response to antigen. Upregulation is a process that activates or increases the rate or extent of that particular response.

Once the macrophage ingests the antigen (Ag) by phagocytosis, endocytosis or macropinocytosis, the Ag is broken down into smaller peptide fractions. These fractions are then bound to MHC, which migrates to the surface of the cell and "presents" the antigen to T cells. This antigen presentation is a necessary step to drive the immune response. Therefore, the ability to increase the levels of MHC class II on macrophages is predictive of an enhanced antigen presentation capacity.

Figure 2:
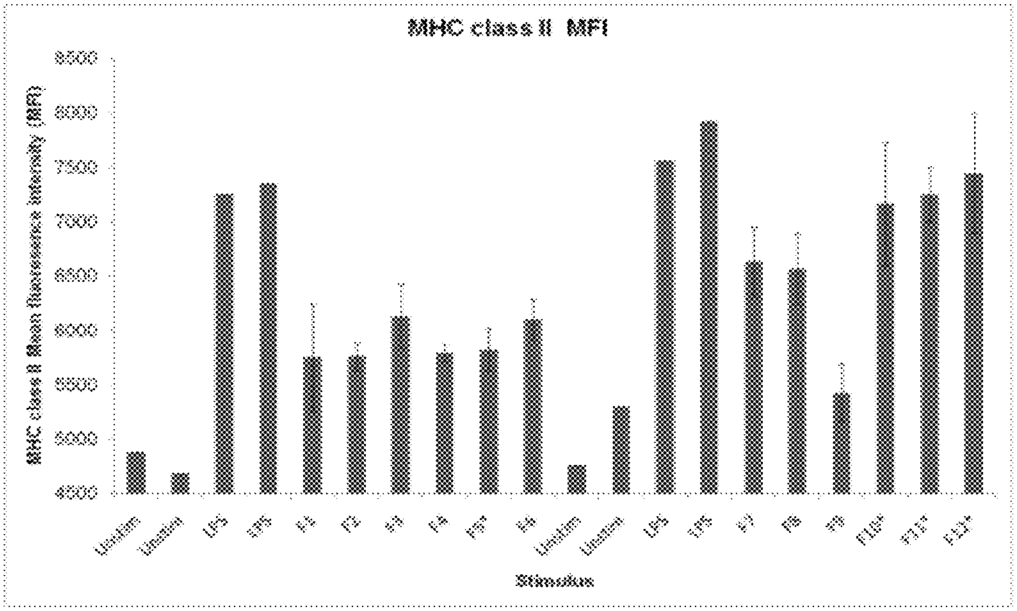
FIG. 2 shows the results of major histocompatibility complex (MHC) Class II Mean Fluorescence Intensity (MFI) analysis from an in-vitro study using murine splenic macrophages in culture.

The data in FIG. 2 shows that all formulations (except F9) enhance the expression of MHC class II, producing significantly higher levels of mean fluorescence intensity than unstimulated controls and the favorable levels compared to the positive controls (LPS).

2. CD25

CD25 is a part of the receptor for IL-2. The upregulation of this molecule is an acute response to activation stimuli that is indicative of a heightened activation state and readiness to function as antigen presenting cells.

Figure 3:
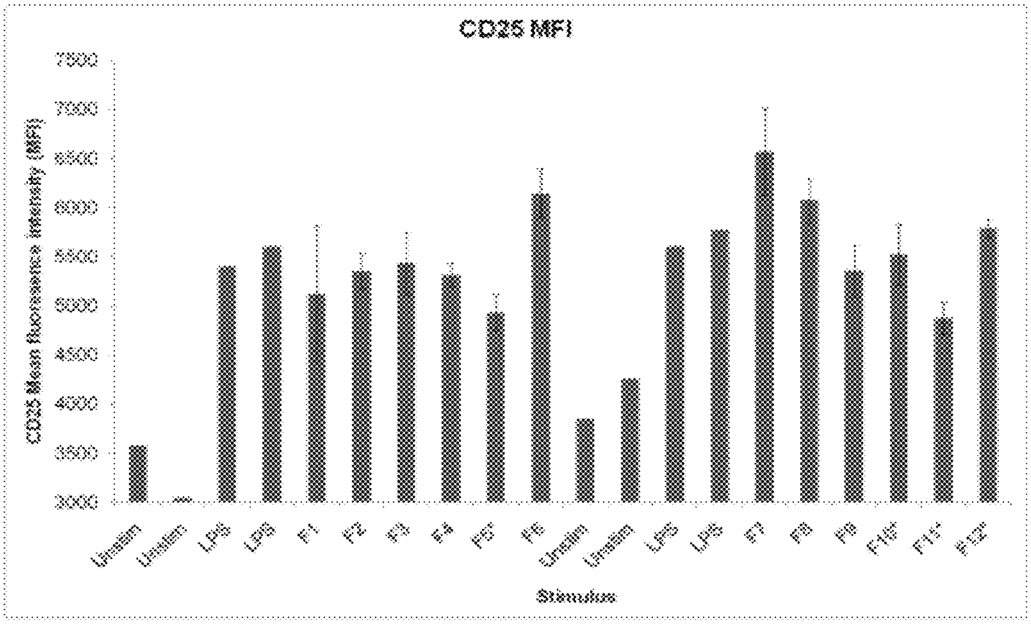
FIG. 3 shows the results of CD25 MFI analysis from an in-vitro study using murine splenic macrophages in culture.

Once presented to naïve T cells, certain co-stimulatory factors and cytokines influence T cell differentiation and expansion. As shown in FIG. 3, all formulations exhibit a greater response than the unstimulated control and a comparable response to the positive controls (LPS). Formulation 6 (containing Tween 80 (polysorbate 80)) and Formulation 7 (containing Poloxamer 188) show an increased response over the positive controls.

3. CD86

CD86 is a costimulatory factor influencing both helper T cells and cytotoxic T cells (necessary for cell mediated immunity). CD86 provides a critical second signal required in order to activate both helper and cytotoxic T cell responses. It is normally expressed at very low levels on resting antigen presenting cells and its upregulation is a critical event in enabling such cells to interact productively with T cells in order to generate an immune response.

Figure 4:
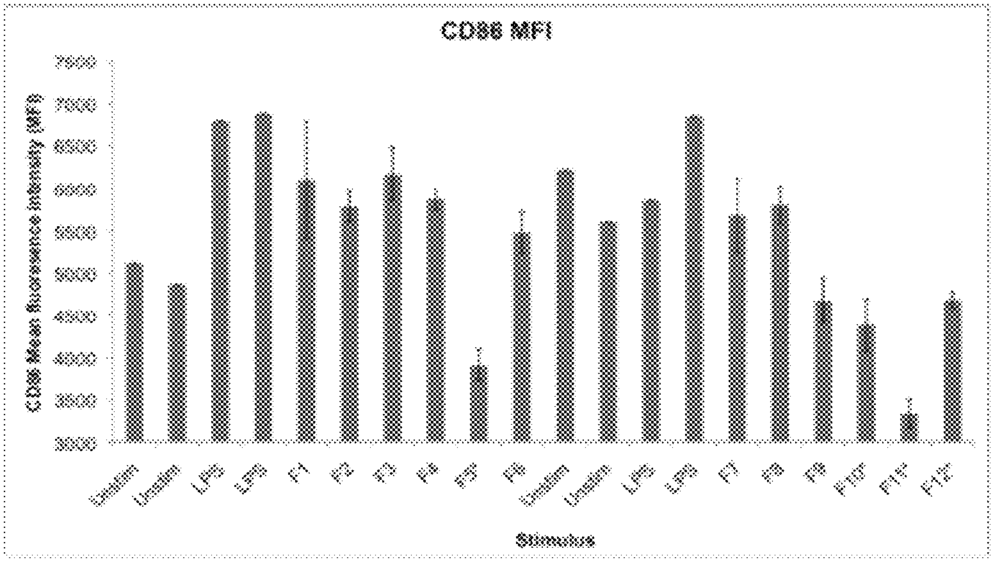
FIG. 4 shows the results of CD86 MFI analysis from an in-vitro study using murine splenic macrophages in culture.

As shown in FIG. 4, all formulations, except those processed at 50° C. (Formulations 5, 10, 11, 12) and the formulation containing lecithin (Formulation 9), were capable of stimulating increased expression of CD86, providing a good response compared to positive controls.

4. Cytokine Profile

The cytokine profile evaluates the cytokine response, which is critical in stimulating and affecting the nature of the T cell response.

The data demonstrates the immune potentiating capability of the starch-based formulations and also the capability to drive T cell responses, i.e., stimulation and expansion (increased population of) T cells.

Presence of TNFalpha and IL12p40 (as a measure of IL-12) are important in driving Th1 and cytoxic T cell responses, whereas IL-4 favors differentiation of T cells into Th2 cells, whose primary role is in stimulating antibody production. IL-6 is involved both in the generation of Th17 responses, which are involved in promoting neutrophil activation, an aspect that is important in mediating protection in certain diseases, and also in promoting the production of antibodies by B cells. IL-10 has the ability to down regulate other immune responses. Down regulation is a process that reduces the activation or rate or extent of activation of a response.

Figure 5:
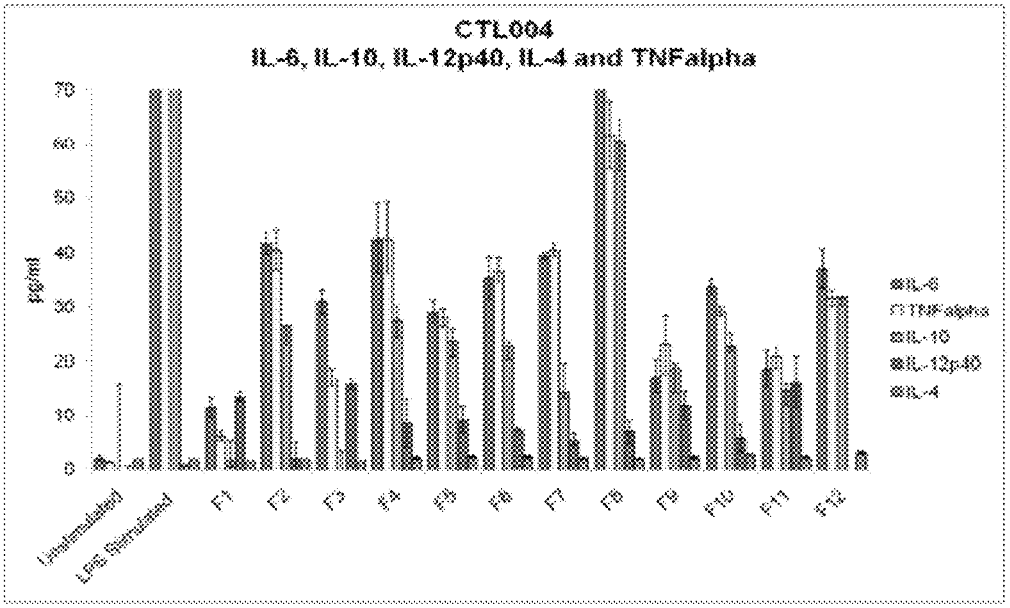
FIG. 5 shows the results of a cytokine profile analysis from an in-vitro study using murine splenic macrophages in culture.

As shown in FIG. 5, all formulations exhibit a significant increase in response in IL-6, TNFalpha and IL-12p40 compared to the unstimulated control. Formulation 1, containing the lowest level of Ag (1 ug) and starch (2.0%), exhibited the lowest response in terms of IL-6 and TNFalpha, though levels of IL-12p40 were comparable to or greater than other formulations.

Increasing the Ag level alone while maintaining a low level of starch (2%), as in Formulation 2, results in an increase in IL-6 and TNFalpha, but IL-12p40 response is relatively low.

Increasing the level of starch with a low level of antigen, as in Formulation 3, increases IL-6 and TNFalpha and produces IL-12p40 response comparable to Formulation 1. This demonstrates the immune potentiating properties of starch. Formulations 1 to 9 comprise hydroxyl propyl starch whereas Formulation 10 comprises corn starch, Formulation 11 comprises waxy maize starch and Formulation 12 comprises rice starch. The data shows that the different sources of starch can exert the same immune potentiating effect.

Increasing the level of both antigen and starch, as in Formulation 4, shows an unexpectedly superior improved response with respect to IL-6, TNFalpha and IL-12p40.

Formulation 8 includes xanthan gum and exhibits greater responses than the other formulations with respect to IL-6 and TNFalpha.

All formulations exhibit low levels of IL-4. The presence of IL-4 very early in immune responses pre-disposes away from Th1 and CTL responses. Therefore, low levels of IL-4 are favorable in terms of establishing a CTL response. IL-4 is important in providing a stimulus toward the generation of Th2 cells, which are, in turn, important for the promotion of antibody responses. Low levels of IL-4 are sufficient for this purpose and other cell types are known to contribute toward its production.

All formulations exhibit higher levels of IL-10 relative to the unstimulated control. IL-10 can down regulate CTL response and favor Th2 response. However, the positive control, LPS, also exhibits high levels of IL-10 and yet this is known to be a potent activator of antigen presenting cells.

B. In Vivo Testing

1. Testing of Example 1 and Comparative Examples 1-3

Blood samples taken from mice at days 14, 28 and 59 were investigated for the presence of Flu-specific IgG in each of the animal groups which were given one of the five formulations and in an untreated animal group (negative control). The graphs in FIG. 1 show antibody levels against influenza virus following 1, 2 and 3 immunizations with different formulations. All graphs display the group mean end point titres (EPT)+/−SEM (n=8 per group).

As shown in FIG. 1, the Zydis® formulation having the novel matrix formulation of Example 1 exhibits higher EPT values at 14, 28 and 59 days than all of the comparative examples and the untreated mice. The group treated with novel matrix tablets plus 1 μg flu were the only animals that exhibited antibody responses above background on days 14 and 28. Further, the end point titre (EPT) of this response increased from day 14 to day 28 to day 59, with increasing immunizations.

2. Testing of Example 2

Based on the results of the in-vitro study shown in Example 2 using macrophage cultures, certain formulations were selected for an in-vivo challenge study in mice. The formulations selected were: F8 (containing xanthan gum); F7 (containing poloxamer 188); F10 (containing corn starch); F4 (containing HP starch); and F12 (containing rice starch).

Five groups of female BALB/c mice were immunized on days 0, 10 and 20 with a test formulation as shown in Table 1. On day 27, the animals were bled for serum analysis and then received a 50 μl intranasal (i.n.) challenge with a/Puerto Rico/8/34 (PR8) H1N1 influenza virus. The animals were monitored for signs of infection over 7 days and scored according to a validated scoring system. Table 4 shows the administration schedule for the formulations.

TABLE 4

| Mice Group | Formulation | Administration Frequency |
|---|---|---|
| 1 | F8 | Once on days 0, 10 and 20 |
| 2 | F7 | Once on days 0, 10 and 20 |
| 3 | F10 | Once on days 0, 10 and 20 |
| 4 | F4 | Once on days 0, 10 and 20 |
| 5 | F12 | Once on days 0, 10 and 20 |

Results

Figure 6:
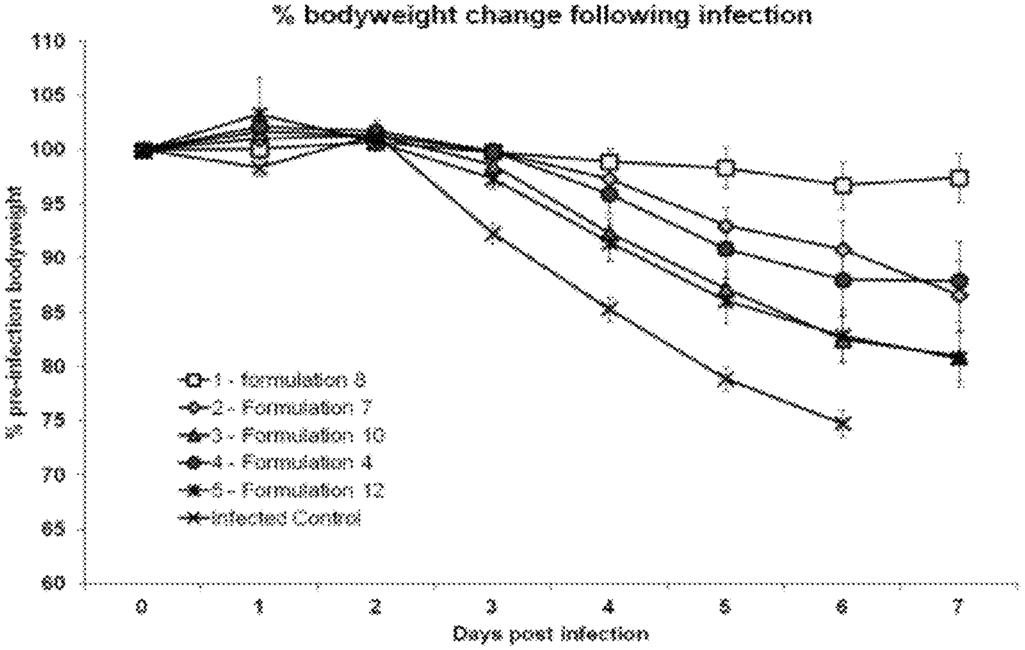
FIG. 6 shows change in bodyweight following immunization and infection of mice in the in-vivo testing.

The body weight of each group of mice was monitored for 7 days following challenge. The results are presented in FIG. 6.

Animals infected with H1N1 PR8 without immunization (infected control) lose weight rapidly from day 3 post infection, reaching an agreed Home Office (HO) endpoint for weight loss of 20% by day 6. All animals immunized with one of the formulations containing influenza antigens showed reduced weight loss. In particular, animals receiving antigen in Formulations 8, 7 and 4, showed a significantly reduced weight loss ($P<0.001$, $P<0.01$ and $P<0.05$, respectively, according to One-way ANOVA and Bonferroni's Multiple Comparison Test).

To compare extent of disease, animals were scored as 0, 0.5 or 1 (no clinical signs, mild clinical signs and moderate clinical signs, respectively) for each of the following parameters, giving a possible maximum score of 5;

Pilo-erection

Hunched posture

Erratic breathing

Mobility effected

Runny eyes

Figure 7:
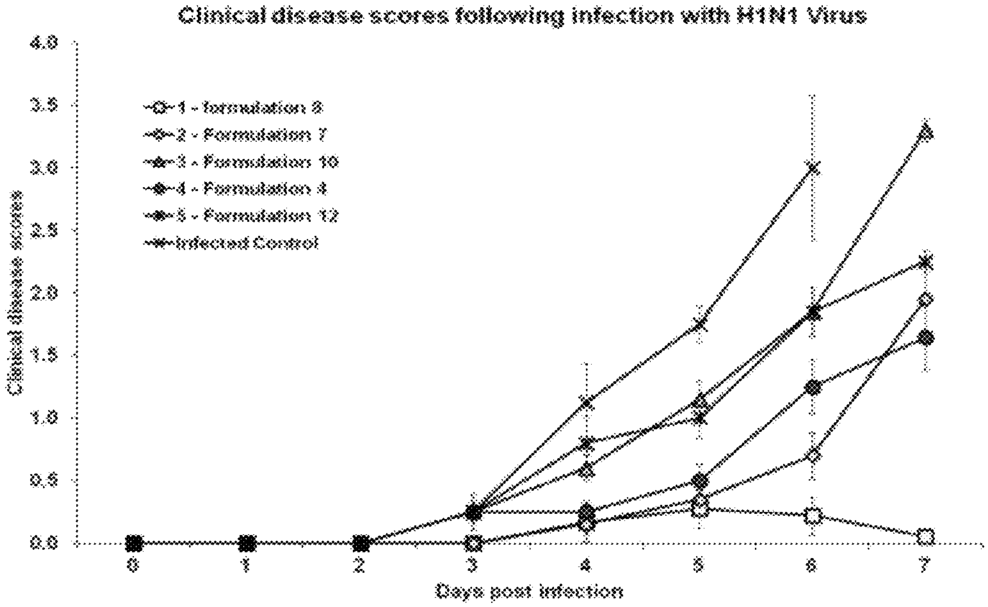
FIG. 7 shows clinical disease scores following immunization and infection of mice in the in-vivo testing.

The scores were charted against time of days post infection and are shown in FIG. 7. As with the weight loss data, all formulations performed better than the infected, unimmunized control. The clinical disease scores also show significant reduction in severity between groups receiving formulations 8, 7 and 4 compared with infected only control, up to day six post infection ($P<0.01$ and $P<0.05$ respectively).

Figure 8:
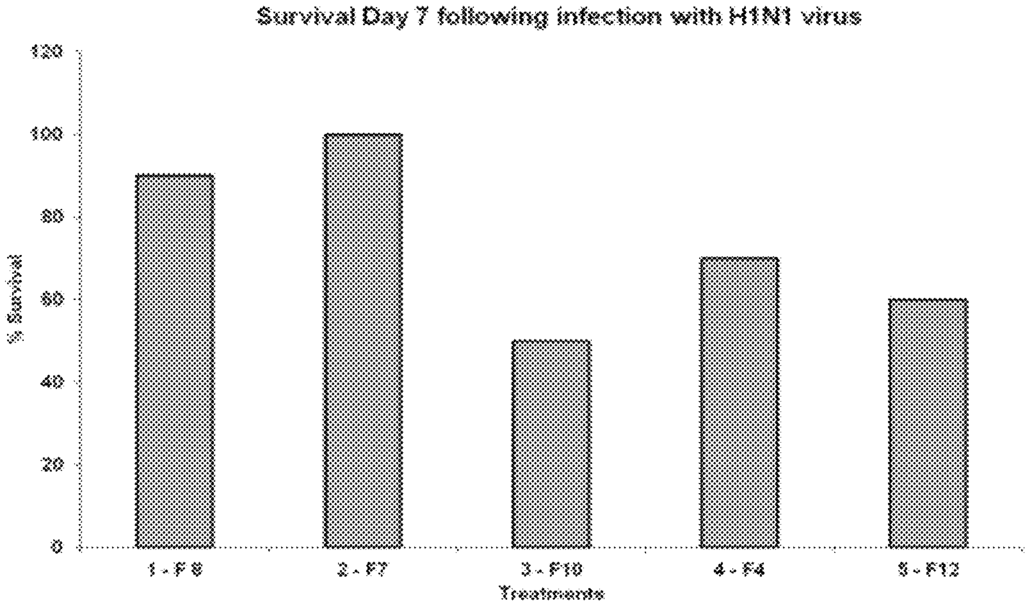
FIG. 8 shows the survival rate after 7 days of mice infected and immunized in the in-vivo testing.

Due to loss of weight and onset of clinical disease, several animals reached the Home Office (HO) humane endpoint prior to day 7 and required termination on day 6. FIG. 8 shows the survival rate at day 7 after immunization with one of the 5 formulations and infection with H1N1 virus. It can be seen that 50% of animals treated with Formulation 10, 70% treated with Formulation 4, and 60% of animals treated with Formulation 12 survived to day 7. Only one animal treated with Formulation 8 had to be terminated on day 6 and none receiving Formulation 7 had to be terminated on day 6.

Figure 9:
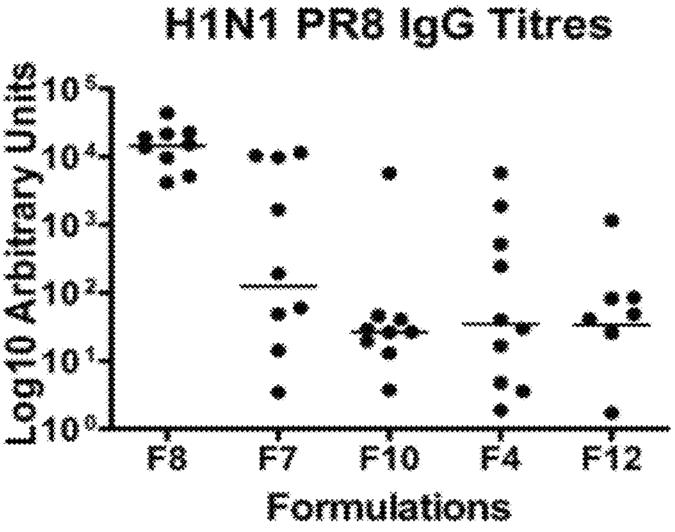
FIGS. 9 through 11 show IgG, IgG1, and IgG2a antibody responses to formulations of Example 2.
Figure 10:
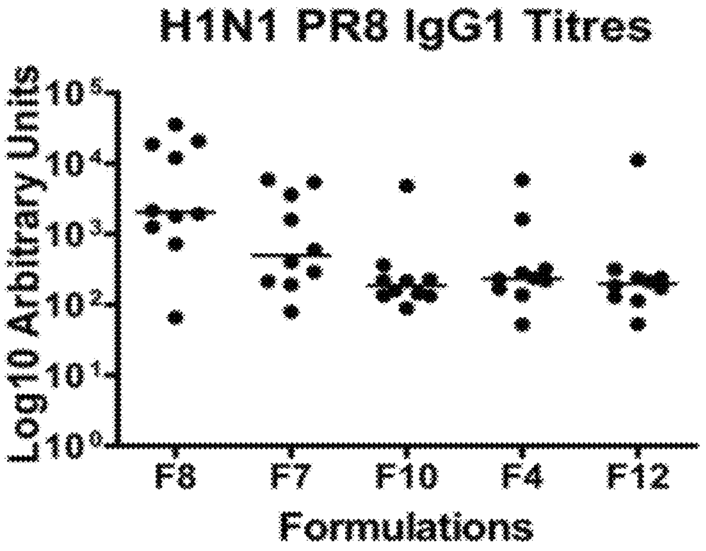
Figure 11:
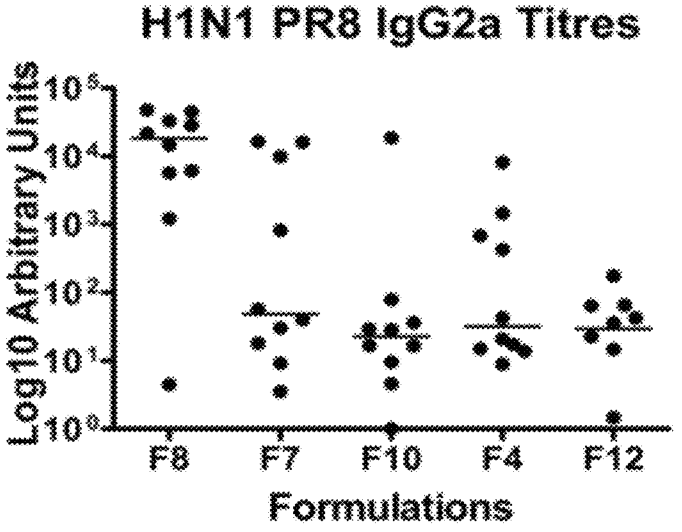

Samples of serum derived from bleeds taken on day 27 were analyzed by ELISA using killed influenza virus as the capture antigen and either mouse IgG, IgG1 or IgG2a as the detecting antibody. The results are shown in FIGS. 9, 10 and 11. Treatments with each of the selected formulations exhibit IgG1 and IgG2a antibody response. Treatment of animals with Formulation 8 stimulated significantly higher titres of anti-H1N1 antibody compared with other treatment groups, Formulations 7, 10, 4 and 12, resulting in high IgG titres ($P<0.01$), in particular the IgG2a isotype ($P<0.001$) when compared by one-way ANOVA and Benferonni's multiple comparison test). The data supports the clinical findings reported above (i.e., body weight, clinical disease scores, and survival rate) demonstrating that the selected formulations can illicit an appropriate and protective immune response.

Figure 12:
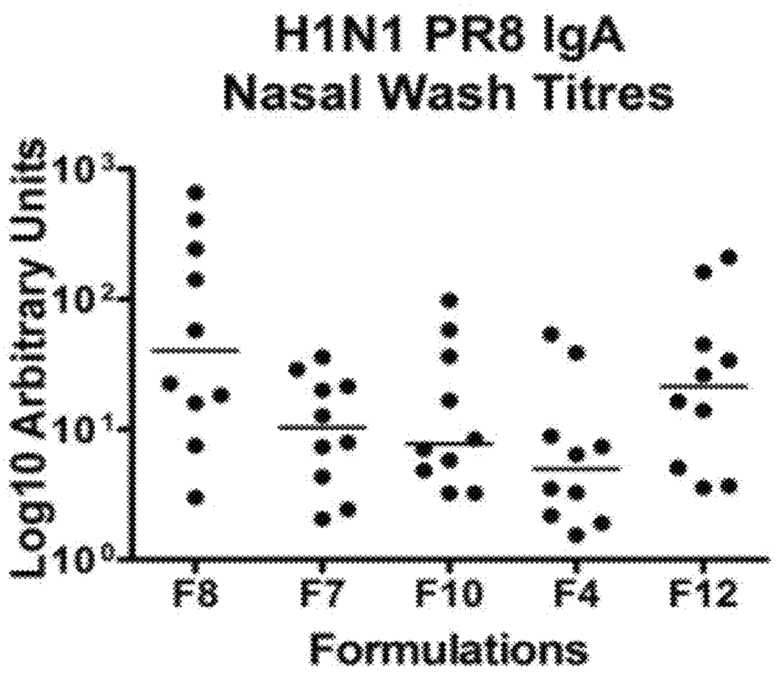
FIG. 12 shows mucosal antibody responses through analysis of nasal washes.

FIG. 12 shows the IgA response from nasal washes taken at the end of the in-vivo challenge study. At that time, the mice were terminated and nasal washes analyzed for IgA as an indicator of mucosal antibody response. The results demonstrated that all formulations were capable of stimulating a mucosal response, with Formulations 8 and 12 giving the highest mean titre values.

Thus, there are numerous advantages to the formulation comprising a starch as an immune response potentiating matrix forming agent for the manufacture of FDDFs of oral vaccines. The resulting FDDF has the unexpected technical advantage of increased immunity response to bacterial and viral infection, which is not known or suggested in the prior art.

Numerous alterations, modifications, and variations of the preferred embodiments disclosed herein will be apparent to those skilled in the art, and they are all anticipated and contemplated to be within the spirit and scope of the claimed invention. For example, although specific embodiments have been described in detail, those with skill in the art will understand that the preceding embodiments and variations can be modified to incorporate various types of substitute, additional or alternative materials. Accordingly, even though only few variations of the present invention are described herein, it is to be understood that the practice of such additional modifications and variations and the equivalents thereof, are within the spirit and scope of the invention as defined in the following claims. All patent applications, patents, and other publications cited herein are incorporated by reference in their entirety.

What is claimed is:

1. A fast-dissolving oral solid vaccine dosage form comprising:

(a) an immunogenic amount of an antigenic preparation;

(b) at least one immune response potentiating matrix forming agent; and (c) at least one additional matrix forming agent, wherein the at least one immune response potentiating matrix forming agent is a starch processed at a temperature of at least about 70° C., wherein the starch is in an amount of 5% to 80% by weight, wherein the at least one additional matrix forming agent is selected from the group consisting of mannitol, gelatin or a combination of mannitol and gelatin, wherein, when present, the gelatin is in an amount of 2.5% to 65% by weight, and the mannitol is in an amount of 5% to 80% by weight, and wherein the dosage form facilitates oral cavity uptake of an antigen within said antigenic preparation.

2. The fast-dissolving oral solid vaccine dosage form according to claim 1, wherein the starch is selected from the group consisting of native starch, modified starch, and combinations thereof.

3. The fast-dissolving oral solid vaccine dosage form according to claim 1, wherein the dosage form disintegrates within 60 seconds after being placed in the oral cavity.

4. The fast-dissolving oral solid vaccine dosage form according to claim 3, wherein the dosage form disintegrates within 30 seconds of being placed in the oral cavity.

5. The fast-dissolving oral solid vaccine dosage form according to claim 4, wherein the dosage form disintegrates within 10 seconds of being placed in the oral cavity.

6. The fast-dissolving oral solid vaccine dosage form according to claim 5, wherein the dosage form disintegrates within 5 seconds of being placed in the oral cavity.

7. The fast-dissolving oral solid vaccine dosage form according to claim 1, prepared by freeze-drying.

8. The fast-dissolving oral solid vaccine dosage form according to claim 1, wherein the at least one additional matrix forming agent is mannitol.

9. The fast-dissolving oral solid vaccine dosage form according to claim 1, wherein the at least one additional matrix forming agent is gelatin.

10. The fast-dissolving oral solid vaccine dosage form according to claim 1, wherein the at least one additional matrix forming agent comprises gelatin and mannitol.

11. The fast-dissolving oral solid vaccine dosage form according to claim 1, wherein the starch is present in an amount of 7% to 75% by weight.

12. The fast-dissolving oral solid vaccine dosage form according to claim 1, wherein the gelatin is present in an amount of 3% to 55%; the mannitol is present in an amount of 7% to 65%; and the starch is present in an amount of 7% to 75% by weight.

13. The fast-dissolving oral solid vaccine dosage form according to claim 1, wherein the at least one additional matrix forming agent further comprises a gum.

14. The fast-dissolving oral solid vaccine dosage form according to claim 13, wherein the gum is xanthan gum.

15. The fast-dissolving oral solid vaccine dosage form according to claim 1, further comprising a surfactant.

16. The fast-dissolving oral solid vaccine dosage form according to claim 15, wherein the surfactant is selected from the group consisting of polysorbate 80 and poloxamer.

17. The fast-dissolving oral solid vaccine dosage form according to claim 1, further comprising an adjuvant.

18. The fast-dissolving oral solid vaccine dosage form according to claim 1, further comprising a mucoadhesive.

19. The fast-dissolving oral solid vaccine dosage form according to claim 1, wherein an immune response is induced when administered to a patient by placement in the oral cavity.

20. The fast-dissolving oral solid vaccine dosage form according to claim 19, wherein placement in the oral cavity is placement on or under the tongue or in the buccal or pharyngeal region.

21. A fast-dissolving oral solid vaccine dosage form comprising:

(a) an immunogenic amount of inactivated influenza virus;
(b) at least one immune response potentiating matrix forming agent; and
(c) at least one additional matrix forming agent, wherein the at least one immune response potentiating matrix forming agent is a starch processed at a temperature of at least about 70° C., wherein the starch is in an amount of 5% to 80% by weight, wherein the at least one additional matrix forming agent is selected from the group consisting of mannitol, gelatin or a combination of mannitol and gelatin, wherein, when present, the gelatin is in an amount of 2.5% to 65% by weight, and the mannitol is in an amount of 5% to 80% by weight, and wherein the dosage form facilitates oral cavity uptake of the inactivated influenza virus.

22. The fast-dissolving oral solid vaccine dosage form according to claim 21, wherein the starch is selected from the group consisting of native starch, modified starch, and combinations thereof.

23. The fast-dissolving oral solid vaccine dosage form according to claim 21, wherein the dosage form disintegrates within 60 seconds after being placed in the oral cavity.

24. The fast-dissolving oral solid vaccine dosage form according to claim 23, wherein the dosage form disintegrates within 30 seconds of being placed in the oral cavity.

25. The fast-dissolving oral solid vaccine dosage form according to claim 24, wherein the dosage form disintegrates within 10 seconds of being placed in the oral cavity.

26. The fast-dissolving oral solid vaccine dosage form according to claim 25, wherein the dosage form disintegrates within 5 seconds of being placed in the oral cavity.

27. The fast-dissolving oral solid vaccine dosage form according to claim 21, prepared by freeze-drying.

28. The fast-dissolving oral solid vaccine dosage form according to claim 21, wherein the at least one additional matrix forming agent is mannitol.

29. The fast-dissolving oral solid vaccine dosage form according to claim 21, wherein the at least one additional matrix forming agent is gelatin.

30. The fast-dissolving oral solid vaccine dosage form according to claim 21, wherein the at least one additional matrix forming agent comprises gelatin and mannitol.

31. The fast-dissolving oral solid vaccine dosage form according to claim 30, wherein the starch is present in an amount of 7% to 75% by weight.

32. The fast-dissolving oral solid vaccine dosage form according to claim 31, wherein the gelatin is present in an amount of 3% to 55%; the mannitol is present in an amount of 7% to 65%; and the starch is present in an amount of 7% to 75% by weight.

33. The fast-dissolving oral solid vaccine dosage form according to claim 21, wherein the at least one additional matrix forming agent further comprises a gum.

34. The fast-dissolving oral solid vaccine dosage form according to claim 33, wherein the gum is xanthan gum.

35. The fast-dissolving oral solid vaccine dosage form according to claim 21, further comprising a surfactant.

36. The fast-dissolving oral solid vaccine dosage form according to claim 35, wherein the surfactant is selected from the group consisting of polysorbate 80 and poloxamer.

37. The fast-dissolving oral solid vaccine dosage form according to claim 21, further comprising an adjuvant.

38. The fast-dissolving oral solid vaccine dosage form according to claim 21, further comprising a mucoadhesive.

39. The fast-dissolving oral solid vaccine dosage form according to claim 21, wherein an influenza specific IgG response is induced when administered to a patient by placement in the oral cavity.

40. The fast-dissolving oral solid vaccine dosage form according to claim 39, wherein placement in the oral cavity is placement on or under the tongue or in the buccal or pharyngeal region.

41. A method of inducing an immune response in a patient, said method comprising the step of:

placing the fast-dissolving oral solid vaccine dosage form of claim 1 in the oral cavity of a person in need of the immune response.

42. The method of inducing an immune response in a patient according to claim 41, wherein placement in the oral cavity is placement on or under the tongue or in the buccal or pharyngeal region.

43. A method of inducing an influenza specific antibody response in a patient, said method comprising the step of:

placing the fast-dissolving oral solid vaccine dosage form of claim 21 in the oral cavity of a person in need of the influenza specific antibody response.

44. The method of inducing an influenza specific antibody response in a patient according to claim 43, wherein placement in the oral cavity is placement on or under the tongue or in the buccal or pharyngeal region.

45. The method of inducing an influenza specific antibody response in a patient according to claim 43, wherein the influenza specific antibody response is an IgG response.

46. A fast-dissolving oral solid vaccine dosage form comprising:

(a) an immunogenic amount of an antigenic preparation;
(b) at least one immune response potentiating matrix forming agent; and
(c) at least one additional matrix forming agent, wherein the at least one immune response potentiating matrix forming agent is a starch processed at a temperature of at least about 70°-75° C., wherein the starch is in an amount of 5% to 80% by weight, wherein the at least one additional matrix forming agent is selected from the group consisting of mannitol, gelatin or a combination of mannitol and gelatin, wherein, when present, the gelatin is a mammalian gelatin, wherein, when present, the gelatin is in an amount of 2.5% to 65% by weight, and the mannitol is in an amount of 5% to 80% by weight, and wherein the dosage form facilitates oral cavity uptake of an antigen within said antigenic preparation.

* * * * *